United States Patent
Liu et al.

(10) Patent No.: US 11,820,846 B2
(45) Date of Patent: Nov. 21, 2023

(54) COMPOSITION, METHOD OF PREPARING COPOLYMER, AND METHODS AND END USES THEREOF

(71) Applicants: Dow Silicones Corporation, Midland, MI (US); Dow Toray Co., Ltd., Tokyo (JP)

(72) Inventors: Nanguo Liu, Midland, MI (US); Tatsuo Souda, Tokyo (JP); Tsunehito Sugiura, Tokyo (JP)

(73) Assignees: DOW SILICONES CORPORATION, Midland, MI (US); DOW TORAY CO., LTD., Tokyo (JP)

( * ) Notice: Subject to any disclaimer, the term of this patent is extended or adjusted under 35 U.S.C. 154(b) by 113 days.

(21) Appl. No.: 17/418,954

(22) PCT Filed: Dec. 27, 2019

(86) PCT No.: PCT/US2019/068805
§ 371 (c)(1),
(2) Date: Jun. 28, 2021

(87) PCT Pub. No.: WO2020/142388
PCT Pub. Date: Jul. 9, 2020

(65) Prior Publication Data
US 2022/0112322 A1    Apr. 14, 2022

Related U.S. Application Data

(60) Provisional application No. 62/786,979, filed on Dec. 31, 2018.

(51) Int. Cl.
*C08F 230/08* (2006.01)
*C08L 83/10* (2006.01)
*C08G 77/20* (2006.01)
*C08G 77/442* (2006.01)

(52) U.S. Cl.
CPC ............ *C08F 230/08* (2013.01); *C08G 77/20* (2013.01); *C08L 83/10* (2013.01); *A61K 2800/10* (2013.01); *C08G 77/442* (2013.01)

(58) Field of Classification Search
CPC ............................ C08F 230/08; C08G 77/442
See application file for complete search history.

(56) References Cited

U.S. PATENT DOCUMENTS

| | | | |
|---|---|---|---|
| 3,794,736 A | 2/1974 | Abbott et al. | |
| 4,127,872 A | 11/1978 | Shen Lo | |
| 4,242,483 A | 12/1980 | Novicky | |
| 4,644,046 A | 2/1987 | Yamada | |
| 4,657,959 A | 4/1987 | Bryan et al. | |
| 4,940,766 A | 7/1990 | Gay et al. | |
| 5,994,488 A | 11/1999 | Yokota et al. | |
| 6,420,504 B1 | 7/2002 | Yoshitake et al. | |
| 7,317,117 B2 | 1/2008 | Nakamura et al. | |
| 10,047,199 B2 | 8/2018 | Iimura et al. | |
| 2007/0142583 A1 | 6/2007 | Schorzman et al. | |
| 2007/0161810 A1 | 7/2007 | Schorzman et al. | |
| 2008/0003195 A1 | 1/2008 | Arnaud et al. | |
| 2008/0293958 A1 | 11/2008 | Bauer et al. | |
| 2011/0104222 A1 | 5/2011 | Iida et al. | |
| 2012/0177402 A1 | 7/2012 | Taniguchi et al. | |
| 2015/0216787 A1 | 8/2015 | Hori et al. | |
| 2015/0232601 A1 | 8/2015 | Furukawa et al. | |
| 2015/0252125 A1 | 9/2015 | Moro et al. | |
| 2016/0108066 A1 | 4/2016 | Goto | |
| 2018/0078486 A1 | 3/2018 | Kadlec et al. | |

(Continued)

FOREIGN PATENT DOCUMENTS

| | | |
|---|---|---|
| CN | 101321772 A | 12/2008 |
| CN | 101356201 A | 1/2009 |

(Continued)

OTHER PUBLICATIONS

Machine assisted English translation of CN102382211A,, obtained from https://patents.google.com on Oct. 4, 2021, 8 pages.
Machine assisted English translation of CN104610337, obtained from https://patents.google.com on Oct. 4, 2021, 9 pages.
Machine assisted English translation of CN104910200, obtained from https://patents.google.com on Oct. 4, 2021, 8 pages.
Machine assisted English translation of DE4234846, obtained from https://patents.google.com on Oct. 4, 2021, 6 pages.
Machine assisted English translation of JP2011126807 obtained from https://patents google.com on Oct. 5, 2021, 10 pages.
Machine assisted English translation of JP2011126808 obtained from https://patents.google.com on Oct. 5, 2021, 8 pages.
Machine assisted English translation of JP2014034568 obtained from https://patents.google.com on Oct. 5, 2021, 11 pages.
Machine assisted English translation of JP2014227388 obtained from https://patents.google.com on Oct. 5, 2021, 9 pages.
Machine assisted English translation of JP2014227358 obtained from https://patents.google.com on Oct. 5, 2021, 10 pages.
Machine assisted English translation of JP2015137252 obtained from https://patents.google.com on Oct. 5, 2021, 12 pages.

(Continued)

*Primary Examiner* — Marc S Zimmer
(74) *Attorney, Agent, or Firm* — WARNER NORCROSS + JUDD LLP

(57) ABSTRACT

A composition comprises: a branched organosilicon compound; an acrylate-functional compound other than the branched organosilicon compound; and optionally a carrier vehicle. The branched organosilicon compound has the following general formula (I): $(R^1)_3Si$—X (I); where X comprises a acryloxy-functional moiety, and each $R^1$ is selected from —$OSi(R^4)_3$ and R, with the proviso that at least one $R^1$ is —$OSi(R^4)_3$; where each R is a substituted or unsubstituted hydrocarbyl group; where each $R^4$ is selected from R, —$OSi(R^5)_3$, and —$[OSiR_2]_m OSiR_3$; where each $R^5$ is selected from R, —$OSi(R^6)_3$, and —$[OSiR_2]_m OSiR_3$; where each $R^6$ is selected from R and —$[OSiR_2]_m OSiR_3$; with the proviso that at least one of $R^4$, $R^5$ and $R^6$ is —$[OSiR_2]_m OSiR_3$; and where $0 \leq m \leq 100$. A method of preparing a copolymer is further provided.

11 Claims, No Drawings

(56) References Cited

U.S. PATENT DOCUMENTS

| | | |
|---|---|---|
| 2019/0053999 A1 | 2/2019 | Hori et al. |
| 2020/0222300 A1 | 7/2020 | Souda et al. |
| 2020/0247928 A1 | 8/2020 | Souda et al. |
| 2021/0032804 A1 | 2/2021 | Hamajima et al. |

FOREIGN PATENT DOCUMENTS

| | | |
|---|---|---|
| CN | 102382211 A | 3/2012 |
| CN | 104610337 A | 5/2015 |
| CN | 104910200 A | 9/2015 |
| CN | 107666899 A | 2/2018 |
| DE | 4234846 A1 | 4/1994 |
| EP | 0281718 A2 | 9/1988 |
| EP | 0739947 A2 | 10/1996 |
| EP | 2582453 B1 | 12/2016 |
| EP | 3208322 B1 | 3/2020 |
| GB | 2119951 B | 9/1986 |
| JP | H01319518 A | 12/1989 |
| JP | H0736224 A | 2/1995 |
| JP | H07173178 A1 | 7/1995 |
| JP | H07196975 A | 8/1995 |
| JP | H07309714 A | 11/1995 |
| JP | 1995196975 A | 8/1996 |
| JP | H09176172 A | 7/1997 |
| JP | 2000072784 | 3/2000 |
| JP | 2001002732 A | 1/2001 |
| JP | 2001011186 A | 1/2001 |
| JP | 2007320960 A | 12/2007 |
| JP | 2010018612 A | 1/2010 |
| JP | 2011016732 A | 1/2011 |
| JP | 2011016733 A | 1/2011 |
| JP | 2011016734 A | 1/2011 |
| JP | 2011126807 A | 6/2011 |
| JP | 2011126808 A | 6/2011 |
| JP | 2011149017 A | 8/2011 |
| JP | 2012121950 A | 6/2012 |
| JP | 2013001672 A | 1/2013 |
| JP | 2014034568 A | 2/2014 |
| JP | 2014040388 A | 3/2014 |
| JP | 2014040511 A | 3/2014 |
| JP | 2014040512 A5 | 3/2014 |
| JP | 2014227358 A | 12/2014 |
| JP | 2015098451 | 5/2015 |
| JP | 2015137252 A | 7/2015 |
| JP | 2016008200 A | 1/2016 |
| JP | 2016088848 A | 5/2016 |
| JP | 2016121095 A | 7/2016 |
| JP | 2016160191 A | 9/2016 |
| JP | 2018090495 A | 6/2018 |
| WO | 2009056779 A3 | 5/2009 |
| WO | 2009146340 A1 | 12/2009 |
| WO | 2010026538 A1 | 3/2010 |
| WO | 2011051323 A3 | 5/2011 |
| WO | 2011078408 A1 | 6/2011 |
| WO | 2012143344 A1 | 10/2012 |
| WO | 2014087183 A1 | 6/2014 |
| WO | 2014154700 A2 | 10/2014 |
| WO | 2014154701 A2 | 10/2014 |
| WO | 2015092632 A2 | 6/2015 |
| WO | 2015097103 A1 | 7/2015 |
| WO | 2015097110 A1 | 7/2015 |
| WO | 2016030842 A1 | 3/2016 |
| WO | 2017037123 A1 | 3/2017 |
| WO | 2017050699 A1 | 3/2017 |
| WO | 2017050922 A1 | 3/2017 |
| WO | 2017061090 A1 | 4/2017 |
| WO | 2018086139 A1 | 5/2018 |
| WO | 2018111458 A1 | 6/2018 |
| WO | 2018186138 A1 | 10/2018 |
| WO | 2019003897 A1 | 1/2019 |
| WO | 2019003898 A1 | 1/2019 |
| WO | 2019155826 A1 | 8/2019 |

OTHER PUBLICATIONS

Machine assisted English translation of JP2016008200 obtained from https://patents.google.com on Oct. 5, 2021, 10 pages.
Machine assisted English translation of JP2016121095 obtained from https://patents.google.com on Oct. 6, 2021, 10 pages.
Machine assisted English translation of JP2016160191 obtained from https://patents.google.com on Oct. 6, 2021, 11 pages.
Machine assisted English translation of JP2018090495 obtained from https://patents.google.com on Oct. 6, 2021, 10 pages.
Machine assisted English translation of JPH07309714 obtained from https://patents.google.com on Oct. 6, 2021, 6 pages.
Machine assisted English translation of JP1995196975 obtained from https://patents.google.com on Oct. 6, 2021, 6 pages.
Machine assisted English translation of JP2000072784 obtained from https://patents.google.com on Oct. 6, 2021, 11 pages.
Machine assisted English translation of JP2001011186 obtained from https://patents.google.com on Oct. 6, 2021, 5 pages.
Machine assisted English translation of JP2011016732 obtained from https://patents.google.com on Oct. 6, 2021, 10 pages.
Machine assisted English translation of JP2011016733 obtained from https://patents.google.com on Oct. 6, 2021, 9 pages.
Machine assisted English translation of JP2011016734 obtained from https://patents.google.com on Oct. 6, 2021, 9 pages.
Machine assisted English translation of JP2013001672 obtained from https://patents.google.com on Oct. 6, 2021, 10 pages.
Machine assisted English translation of JP2015098451 obtained from https://patents.google.com on Oct. 7, 2021, 11 pages.
Machine assisted English translation of JP2016088848 obtained from https://patents.google.com on Oct. 7, 2021, 11 pages.
Machine assisted English translation of JPH07173178 obtained from https://patents.google.com on Oct. 7, 2021, 10 pages.
Machine assisted English translation of JPH07196975 obtained from https://patents.google.com on Oct. 7, 2021, 8 pages.
Machine assisted English translation of JPH0736224 obtained from https://patents.google.com on Oct. 7, 2021, 4 pages.
Machine assisted English translation of JPH09176172 obtained from https://patents.google.com on Oct. 7, 2021, 10 pages.
Machine assisted English translation of WO2018186138 obtained from https://patents.google.com on Oct. 7, 2021, 22 pages.
Machine assisted English translation of WO2009056779 obtained from https://patents.google.com on Oct. 7, 2021, 3 pages.
Grande, John B., The Piers-Rubinsztajn Reaction: New Routes to Structured Silicones. Diss. 201. 297 pages.
Grande, John B., et al. "Silicone Dendrons and Dendrimers From Orthogonal SiH Coupling Reactions" Polymer Chemistry, 2014, pp. 6728-6739, 5.23.
Hamid Javaherian Naghash et al., Synthesis and Characterization of a Nonionic Copolymeric Surfactant Based on a Monotelechelic Polydimethylsiloxane and Oxypropylated Acrylate Ester, Synthesis and Reactivity in Inorganic, Metal- organic, Nano-metal Chemistry, Apr. 21, 2014, pp. 514-522, Vo;. 44, No. 4.
David Mancardi et al., "Convenient Synthesis of Tributylsilyl Methacrylate," Synthetic Communications, Oct. 1, 2007, pp. 3873-3878, vol. 37, No. 21.
Sangkyu Lee et al., "Refractive Index Engineering of Transparent ZrO2-polydimethylsiloxane Nanocompositves," Journal of Materials Chemistry, Jan. 2018, p. 1751-1755, vol. 18, No. 15.
International Search Report for International Application No. PCT/US2019/0068805, dated Apr. 3, 2020, four pages.
Machine assisted English translation of JPH0319518A obtained from https://patents.google.com on Oct. 7, 2021, 9 pages.
Machine assisted English translation JP2001002732A obtained from https://patents.google.com/patent on May 2, 2022, 13 pages.
Vlachine assisted English translation of JP2012121950A obtained from https://worldwide.espacenet.comtpatent on 5 Jun. 2023, 16 pp.

COMPOSITION, METHOD OF PREPARING COPOLYMER, AND METHODS AND END USES THEREOF

CROSS-REFERENCE TO RELATED APPLICATIONS

This application is the National Stage of International Appl. No. PCT/US2019/068805 filed on 27 Dec. 2019, which claims priority to and all advantages of U.S. Provisional Patent Application No. 62/786,979 filed on 31 Dec. 2018, the content of which is incorporated herein by reference.

FIELD OF THE INVENTION

The present invention generally relates to a composition and, more specifically, to a composition comprising a branched organosilicon compound and an acrylate-functional compound for preparing a copolymer, and to the copolymer formed therewith and related end use applications thereof.

DESCRIPTION OF THE RELATED ART

Silicones are polymeric materials used in numerous commercial applications, primarily due to significant advantages they possess over their carbon-based analogues. More precisely called polymerized siloxanes or polysiloxanes, silicones have an inorganic silicon-oxygen backbone chain ( . . . —Si—O—Si—O—Si—O— . . . ) with organic side groups attached to the silicon atoms.

Organic side groups may be used to link two or more of these backbones together. By varying the —Si—O— chain lengths, side groups, and crosslinking, silicones can be synthesized with a wide variety of properties and compositions. They can vary in consistency from liquid to gel to rubber to hard plastic. The most common siloxane is linear polydimethylsiloxane (PDMS), a silicone oil. The second largest group of silicone materials is based on silicone resins, which are formed by branched and cage-like oligosiloxanes.

Another group of silicone materials are silicone dendrimers. Dendrimers are polymers that have a highly branched structure which extends radially from a single core. A dendrimer is a repetitively branched molecule, typically symmetric (or near symmetric) around the core, and often adopts a spherical or ellipsoidal three-dimensional morphology. Dendritic polymers can also be described as tree-like macromolecules consisting of unique branch-upon-branch-upon-branch structural organizations or generations.

Dendritic silicones or macromolecules have molecular shapes, sizes, and functionality that provide for many potential end applications. Thus, there remains an opportunity to provide improved branched compounds based on silicon, as well as improved methods of forming such compounds. There also remains an opportunity to provide improved copolymers and improved compositions based on or having such compounds.

BRIEF SUMMARY OF THE INVENTION

A composition is provided. The composition comprises: a branched organosilicon compound; an acrylate-functional compound other than the branched organosilicon compound; and optionally a carrier vehicle.

The branched organosilicon compound has the following general formula (I):

where X comprises a acryloxy-functional moiety, and each $R^1$ is selected from —OSi($R^4$)$_3$ and R, with the proviso that at least one $R^1$ is —OSi($R^4$)$_3$; where each R is a substituted or unsubstituted hydrocarbyl group; where each $R^4$ is selected from R, —OSi($R^5$)$_3$, and —[OSi$R_2$]$_m$OSi$R_3$; where each $R^5$ is selected from R, —OSi($R^6$)$_3$, and —[OSi$R_2$]$_m$OSi$R_3$; where each $R^6$ is selected from R and —[OSi$R_2$]$_m$OSi$R_3$; with the proviso that at least one of $R^4$, $R^5$ and $R^6$ is —[OSi$R_2$]$_m$OSi$R_3$; and where 0≤m≤100.

A method of preparing a copolymer is further provided. The method comprises reacting the branched organosilicon compound and the acrylate-functional compound in the presence of the carrier vehicle. A copolymer formed in accordance with the method is further provided. In addition, a film formed with or by the copolymer is provided. Further still, a composition comprising the copolymer and a carrier vehicle is provided.

DETAILED DESCRIPTION OF THE INVENTION

A composition comprises a branched organosilicon compound. The branched organosilicon compound has the following general formula (I):

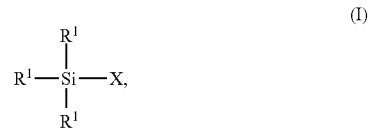

where X comprises an acryloxy-functional moiety, and each $R^1$ is selected from —OSi($R^4$)$_3$ and R, with the proviso that at least one $R^1$ is —OSi($R^4$)$_3$; where each R is a substituted or unsubstituted hydrocarbyl group; where each $R^4$ is selected from R, —OSi($R^5$)$_3$, and —[OSi$R_2$]$_m$OSi$R_3$; where each $R^5$ is selected from R, —OSi($R^6$)$_3$, and —[OSi$R_2$]$_m$OSi$R_3$; where each $R^6$ is selected from R and —[OSi$R_2$]$_m$OSi$R_3$; with the proviso that at least one of $R^4$, $R^5$ and $R^6$ is —[OSi$R_2$]$_m$OSi$R_3$; and where 0≤m≤100.

Each R is independently selected and may be linear, branched, cyclic, or combinations thereof. Cyclic hydrocarbyl groups encompass aryl groups as well as saturated or non-conjugated cyclic groups. Cyclic hydrocarbyl groups may be monocyclic or polycyclic. Linear and branched hydrocarbyl groups may independently be saturated or unsaturated. One example of a combination of a linear and cyclic hydrocarbyl group is an aralkyl group. By "substituted," it is meant that one or more hydrogen atoms may be replaced with atoms other than hydrogen (e.g. a halogen atom, such as chlorine, fluorine, bromine, etc.), or a carbon atom within the chain of R may be replaced with an atom other than carbon, i.e., R may include one or more heteroatoms within the chain, such as oxygen, sulfur, nitrogen, etc. Suitable alkyl groups are exemplified by, but not limited to, methyl, ethyl, propyl (e.g., iso-propyl and/or n-propyl), butyl (e.g., isobutyl, n-butyl, tert-butyl, and/or sec-butyl), pentyl (e.g., isopentyl, neopentyl, and/or tert-pentyl), hexyl, as well as branched saturated hydrocarbon groups of 6 carbon atoms. Suitable aryl groups are exemplified by, but not limited to, phenyl, tolyl, xylyl, naphthyl, benzyl, and dimethyl phenyl. Suitable alkenyl groups include vinyl, allyl, propenyl, isopropenyl, butenyl, isobutenyl, pentenyl, heptenyl, hexenyl, and cyclohexenyl groups. Suitable monovalent halogenated hydrocarbon groups include, but are not limited to, a halogenated alkyl group of 1 to 6 carbon atoms, or a halogenated aryl group of 6 to 10 carbon atoms. Suitable halogenated alkyl groups are exemplified by, but not limited to, the alkyl groups described above where one or more hydrogen atoms is replaced with a halogen atom, such as F or Cl. For example, fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl, 2,2-difluorocyclopropyl, 2,3-difluorocyclobutyl, 3,4-difluorocyclohexyl, and 3,4-difluoro-5-methylcycloheptyl, chloromethyl, chloropropyl, 2-dichlorocyclopropyl, and 2,3-dichlorocyclopentyl are examples of suitable halogenated alkyl groups. Suitable halogenated aryl groups are exemplified by, but not limited to, the aryl groups described above where one or more hydrogen atoms is replaced with a halogen atom, such as F or Cl. For example, chlorobenzyl and fluorobenzyl are suitable halogenated aryl groups.

In specific embodiments, each R is independently an alkyl group having from 1 to 10, alternatively from 1 to 8, alternatively from 1 to 6, alternatively from 1 to 4, alternatively from 1 to 3, alternatively from 1 to 2, alternatively 1, carbon atom(s).

Each $R^1$ is selected from R and $-OSi(R^4)_3$, with the proviso that at least one $R^1$ is $-OSi(R^4)_3$. In certain embodiments, at least two of $R^1$ are $-OSi(R^4)_3$. In specific embodiments, all three of $R^1$ are $-OSi(R^4)_3$. When a greater number of $R^1$ are $-OSi(R^4)_3$, the organosilicon compound has a greater level of branching. For example, when each $R^1$ is $-OSi(R^4)_3$ and the Si—X bond is a silicon-carbon bond, the silicon atom to which each $R^1$ is bonded is a T siloxy unit. Alternatively, when two of $R^1$ are $-OSi(R^4)_3$ and the Si—X bond is a silicon-carbon bond, the silicon atom to which each $R^1$ is bonded is a D siloxy unit.

Each $R^4$ is selected from R, $-OSi(R^5)_3$, and $-[OSiR_2]_m OSiR_3$, where $0 \le m \le 100$. Depending on a selection of $R^4$ and $R^5$, further branching can be present in the branched organosilicon compound. For example, when each $R^4$ is R, then each $-OSi(R^4)_3$ moiety is a terminal M siloxy unit. Said differently, when each $R^1$ is $-OSi(R^4)_3$, and when each $R^4$ is R, then each $R^1$ can be written as $OSiR_3$, and each $R^1$ is an M siloxy unit. In such embodiments, the branched organosilicon compound includes a T siloxy unit (to which X is bonded) capped by three M siloxy units. When $R^4$ is $-[OSiR_2]_m OSiR_3$, $R^4$ includes optional D siloxy units (i.e., those siloxy units in the moiety indicated by subscript m), and an M siloxy unit (represented by $OSiR_3$). Thus, for example, when each $R^1$ is $-OSi(R^4)_3$, and when each $R^4$ is $-[OSiR_2]_m OSiR_3$, then each $R^1$ includes a Q siloxy unit. In such embodiments, each $R^1$ is of formula $-OSi([OSiR_2]_m OSiR_3)_3$. When each m is 0, each $R^1$ is a Q siloxy unit endcapped with three M siloxy units. When m is greater than 0, each $R^1$ includes a linear moiety with a degree of polymerization being attributable to m. This linear moiety, if present, is generally a diorganosiloxane moiety.

Subscript m is from (and including) 0 to 100, alternatively from 0 to 80, alternatively from 0 to 60, alternatively from 0 to 40, alternatively from 0 to 20, alternatively from 0 to 19, alternatively from 0 to 18, alternatively from 0 to 17, alternatively from 0 to 16, alternatively from 0 to 15, alternatively from 0 to 14, alternatively from 0 to 13, alternatively from 0 to 12, alternatively from 0 to 11, alternatively from 0 to 10, alternatively from 0 to 9, alternatively from 0 to 8, alternatively from 0 to 7, alternatively from 0 to 6, alternatively from 0 to 5, alternatively from 0 to 4, alternatively from 0 to 3, alternatively from 0 to 2, alternatively from 0 to 1, alternatively is 0. Typically, each subscript m is 0 such that the branched moiety of the branched organosilicon compound is free from D siloxy units.

As set forth above, each $R^4$ can also be $-OSi(R^5)_3$. In such embodiments, depending a selection of $R^5$, further branching can be present in the branched organosilicon compound. Each $R^5$ is selected from R, $-OSi(R^6)_3$, and $-[OSiR_2]_m OSiR_3$, where m is defined above; where each $R^6$ is selected from R and $-[OSiR_2]_m OSiR_3$, where m is defined above. At least one of $R^4$, $R^5$ and $R^6$ is $-[OSiR_2]_m OSiR_3$, where m is defined above. When $R^1$ is of formula $-OSi(R^4)_3$, and when $R^4$ is of formula $-OSi(R^5)_3$, further siloxane bonds and branching is present in the branched organosilicon compound. This is further the case when $R^5$ is $-OSi(R^6)_3$ In particular, each subsequent R moiety in the branched organosilicon compound can impart a further generation of branching. For example, $R^1$ can be of formula $-OSi(R^4)_3$, $R^4$ can be of formula $-OSi(R^5)_3$, and $R^5$ can be $-OSi(R^6)_3$. Thus, depending on a selection of each substituent, further branching attributable to T and/or Q siloxy units may be present in the branched organosilicon compound.

Importantly, each of R, $R^1$, $R^4$, $R^5$, and $R^6$ are independently selected. As such, the descriptions above relating to each of these substituents is not meant to mean or imply that each substituent is the same. Any description above relating to $R^1$ may relate to only one $R^1$ or any number of $R^1$ in the branched organosilicon compound, and so on.

In addition, different selections of R, $R^1$, $R^4$, $R^5$, and $R^6$ can result in the same structures. For example, if $R^1$ is $-OSi(R^4)_3$, and if each $R^4$ is $-OSi(R^5)_3$, and if each $R^5$ is R, then $R^1$ can be written as $-OSi(OSiR_3)_3$. Similarly, if $R^1$ is $-OSi(R^4)_3$, and if each $R^4$ is $-[OSiR_2]_m OSiR_3$, where m is 0, then $R^1$ can be written as $-OSi(OSiR_3)_3$. This results in the same structure for $R^1$ based on different selections for $R^4$. To that end, at least one of $R^4$, $R^5$ and $R^6$ is $-[OSiR_2]_m OSiR_3$. However, when m is 0, this proviso can be inherently met through alternative selections. For example, as noted above, if each $R^4$ is $-OSi(R^5)_3$, and if each $R^5$ is R, then $R^1$ can be written as $-OSi(OSiR_3)_3$, which is the same as if $R^1$ is $-OSi(R^4)_3$, and if each $R^4$ is $-[OSiR_2]_m OSiR_3$, where m is 0. It shall be considered that the proviso is met even if alternative selections can result in the same structures as required in the proviso.

In certain embodiments, each $R^1$ is $-OSi(R^4)_3$. In specific embodiments in which each $R^1$ is $-OSi(R^4)_3$, at least one $R^4$ is $-[OSiR_2]_m OSiR_3$, where m is 0. Because m is 0, the at least one $R^4$ is $-OSiR_3$. This is the same structure as if at least one $R^4$ is $-OSi(R^5)_3$, and if each $R^5$ is R. Both selections result in at least one $R^4$ being $-OSiR_3$. Thus, if at least one $R^4$ is $-OSi(R^5)_3$, and if each $R^5$ is R, it shall also be considered that at least one of $R^4$ is $-[OSiR_2]_m OSiR_3$, where m is 0.

The same is true for further generations of branching in the branched organosilicon compound. For example, just as different selections associated with $R^4$ and $R^5$ can result in the same structure above, different selections for $R^5$ and $R^6$ can similarly result in the same structure.

In certain embodiments, each $R^1$ is $—OSi(R^4)_3$. In specific embodiments in which each $R^1$ is $—OSi(R^4)_3$, one $R^4$ is R in each $—OSi(R^4)_3$ such that each $R^1$ is $—OSiR(R^4)_2$. In further specific embodiments, two $R^4$ in $—OSiR(R^4)_2$ are each $—OSi(R^5)_3$ moieties such that the branched organosilicon compound has the following structure:

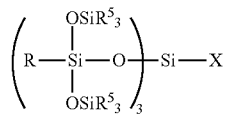

where R is independently selected and defined above, and each $R^5$ is independently selected and defined above, and X is defined above. In certain embodiments, each $R^5$ is R, and each R is methyl.

As noted above, the same structure of the branched organosilicon compound can result from different selections. For example, the same branched organosilicon compound as exemplified above results with the following selections: each $R^1$ is $—OSi(R^4)_3$, where one $R^4$ is R and two of $R^4$ are $—[OSiR_2]_mOSiR_3$, where m is 0. Thus, in the structure exemplified above, the proviso that at least one of $R^4$, $R^5$ and $R^6$ be $—[OSiR_2]_mOSiR_3$ is met regardless of the selections of $R^4$ and $R^5$ utilized to arrive at the resulting structure.

In other embodiments, one $R^1$ is R, and two of $R^1$ are $—OSi(R^4)_3$. In specific embodiments in which two of $R^1$ is $—OSi(R^4)_3$, one $R^4$ is R in each $—OSi(R^4)_3$ such that two of $R^1$ are $—OSiR(R^4)_2$. In further specific embodiments, each $R^4$ in $—OSiR(R^4)_2$ is $—OSi(R^5)_3$ such that the branched organosilicon compound has the following structure:

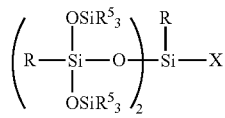

where R is independently selected and defined above, and each $R^5$ is independently selected and defined above, and X is defined above. In certain embodiments, each $R^5$ is R, and each R is methyl.

As noted above, the same structure of the branched organosilicon compound can result from different selections. For example, the same branched organosilicon compound as exemplified above results with the following selections: one $R^1$ is R; two of $R^1$ are $—OSi(R^4)_3$, where one $R^4$ is R and two of $R^4$ are $—[OSiR_2]_mOSiR_3$, where m is 0, in each $—OSi(R^4)_3$. Thus, in the structure exemplified above, the proviso that at least one of $R^4$, $R^5$ and $R^6$ be $—[OSiR_2]_mOSiR_3$ is met regardless of the selections of $R^4$ and $R^5$ utilized to arrive at the resulting structure.

In yet other embodiments, two of $R^1$ are R, and one $R^1$ is $—OSi(R^4)_3$. In specific embodiments in which one of $R^1$ is $—OSi(R^4)_3$, and one $R^4$ is R in $—OSi(R^4)_3$ such that this specific $R^1$ is $—OSiR(R^4)_2$. In further specific embodiments, each $R^4$ in $—OSiR(R^4)_2$ is $—OSi(R^5)_3$ such that the branched organosilicon compound has the following structure:

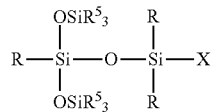

where R is independently selected and defined above, and each $R^5$ is independently selected and defined above, and X is defined above. In certain embodiments, each $R^5$ is R, and each R is methyl.

As noted above, the same structure of the branched organosilicon compound can result from different selections. For example, the same branched organosilicon compound as exemplified above results with the following selections: two of $R^1$ are R; one of $R^1$ is $—OSi(R^4)_3$, where one $R^4$ is R and two of $R^4$ are $—[OSiR_2]_mOSiR_3$, where m is 0, in $—OSi(R^4)_3$. Thus, in the structure exemplified above, the proviso that at least one of $R^4$, $R^5$ and $R^6$ be $—[OSiR_2]_mOSiR_3$ is met regardless of the selections of $R^4$ and $R^5$ utilized to arrive at the resulting structure.

In the exemplary structures set forth above, each $R^5$ is R, and each R is methyl. However, further generational branching can be introduced into the branched organosilicon compound when $R^5$ is other than R, i.e., when $R^5$ is selected from $OSi(R^6)_3$, and $—[OSiR_2]_mOSiR_3$, where m is defined above; where each $R^6$ is selected from R and $—[OSiR_2]_mOSiR_3$, where m is defined above.

As set forth above, X comprises an acryloxy-functional moiety. In certain embodiments, X has formula $-D-R^2$, where D is a divalent linking group and $R^2$ is an acryloxy group.

Each D is an independently selected divalent hydrocarbon group having from 2 to 18 carbon atoms, alternatively from 2 to 16 carbon atoms, alternatively from 2 to 14 carbon atoms, alternatively from 2 to 12 carbon atoms, alternatively from 2 to 10 carbon atoms, alternatively from 2 to 8 carbon atoms, alternatively from 2 to 6 carbon atoms, alternatively from 2 to 4 carbon atoms, alternatively 3 carbon atoms, alternatively 2 carbon atoms. Each D may independently be linear or branched. For example, when D has two carbon atoms, D has formula $C_2H_4$, and may be linear ($CH_2CH_2$) or branched ($CHCH_3$). In certain embodiments, D is linear. In specific embodiments, each D is $C_3H_6$. D may optionally include one or more heteroatoms. For example, in one embodiment, D comprises an ether moiety.

$R^2$ is an acryloxy group of the formula:

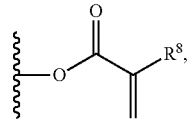

where $R^8$ is independently selected from hydrocarbyl groups and H. In some such embodiments, $R^8$ is H or $—CH_3$.

Acrylate Compound

The composition further comprises an acrylate-functional compound. The acrylate-functional compound is not limited and may any acrylate-functional compound, as described in further detail below. The term "acrylate-functional compound," as used herein, means a compound or molecule including at least one, alternatively at least two, acrylate functional groups (e.g. alkyl acrylate groups such as methyl, ethyl, or butyl acrylate groups, substituted acrylate groups such as a 2-ethylhexyl or hydroxyl ethyl groups, and others such as a methylolpropane acrylate groups, etc.). As will be understood in view of the description herein, the acrylate-functional compound may be monomeric, oligomeric, polymeric, aliphatic, aromatic, araliphatic, etc. In addition, the copolymer may comprise a number of different acrylate-functional groups, which are independently selected.

Acrylate compounds and methods of preparing acrylate-functional compounds are known in the art. For example, polyacrylates may be prepared via a conventional radical polymerization of acrylic monomers. Such conventional methods are generally carried out by combining radically-polymerizable monomers (e.g. acrylate monomers, comonomers, etc.) in the presence of a radical initiator/generator, such as a thermo-, chemo, and/or photopolymerization initiator. For example, peroxides and aromatic initiators (e.g. phenols, benzoins, heterocylcles such as imidazoles, etc.) are commonly utilized. These conventional methods may be used to prepare acrylate homopolymers and copolymers, including ternary, quaternary, and higher-order copolymers. Additionally, di- and/or multifunctional acrylic monomers may also be utilized, e.g. to prepare multifunctional polyacrylates (and polyacrylate compounds), as will be understood in view of the description of suitable acrylic monomers herein.

In general, methods of preparing acrylate-functional compounds utilize at least one acrylic monomer having an acryloyloxy or alkylacryloyloxy group (i.e., acrylates, alkylacrylates, acrylic acids, alkylacrylic acids, and the like, as well as derivatives and/or combinations thereof). Such acrylic monomers may be monofunctional or polyfunctional acrylic monomers.

Examples of specific monofunctional acrylic monomers suitable for preparing polyacrylates (and polyacrylate moieties) include (alkyl)acrylic compounds, such as methyl acrylate, phenoxyethyl (meth)acrylate, phenoxy-2-methylethyl (meth)acrylate, phenoxyethoxyethyl (meth)acrylate, 3-phenoxy-2-hydroxypropyl (meth)acrylate, 2-phenylphenoxyethyl (meth)acrylate, 4-phenylphenoxyethyl (meth)acrylate, 3-(2-phenylphenyl)-2-hydroxypropyl (meth)acrylate, polyoxyethylene-modified p-cumylphenol (meth) acrylate, 2-bromophenoxyethyl (meth)acrylate, 2,4-dibromophenoxyethyl (meth)acrylate, 2,4,6-tribromophenoxyethyl (meth)acrylate, polyoxyethylene-modified phenoxy (meth)acrylate, polyoxypropylene-modified phenoxy (meth)acrylate, polyoxyethylene nonylphenyl ether (meth)acrylate, isobornyl (meth)acrylate, 1-adamantyl (meth)acrylate, 2-methyl-2-adamantyl (meth) acrylate, 2-ethyl-2-adamantyl (meth)acrylate, bornyl (meth) acrylate, tricyclodecanyl (meth)acrylate, dicyclopentanyl (meth)acrylate, dicyclopentenyl (meth)acrylate, cyclohexyl (meth)acrylate, 4-butylcyclohexyl (meth)acrylate, acryloylmorpholine, 2-hydroxyethyl (meth)acrylate, 2-hydroxypropyl (meth)acrylate, 2-hydroxybutyl (meth)acrylate, methyl (meth)acrylate, ethyl (meth)acrylate, propyl (meth) acrylate, isopropyl (meth)acrylate, butyl (meth)acrylate, amyl (meth)acrylate, isobutyl (meth)acrylate, t-butyl (meth) acrylate, pentyl (meth)acrylate, isoamyl (meth)acrylate, hexyl (meth)acrylate, heptyl (meth)acrylate, octyl (meth) acrylate, isooctyl (meth)acrylate, 2-ethylhexyl (meth)acrylate, nonyl (meth)acrylate, decyl (meth)acrylate, isodecyl (meth)acrylate, undecyl (meth)acrylate, dodecyl (meth) acrylate, lauryl (meth)acrylate, stearyl (meth)acrylate, isostearyl (meth)acrylate, benzyl (meth)acrylate, 1-naphthylmethyl (meth)acrylate, 2-naphthylmethyl (meth)acrylate, tetrahydrofurfuryl (meth)acrylate, butoxyethyl (meth)acrylate, ethoxydiethylene glycol (meth)acrylate, poly(ethylene glycol) mono(meth)acrylate, poly(propylene glycol) mono (meth)acrylate, methoxyethylene glycol (meth)acrylate, ethoxyethyl (meth)acrylate, methoxypoly(ethylene glycol) (meth)acrylate, methoxypoly(propylene glycol) (meth)acrylate, diacetone (meth)acrylamide, isobutoxymethyl (meth) acrylamide, N,N-dimethyl (meth)acrylamide, t-octyl (meth) acrylamide, dimethylaminoethyl (meth)acrylate, diethylaminoethyl (meth)acrylate, 7-amino-3,7-dimethyloctyl (meth)acrylate, N,N-diethyl (meth)acrylamide, N,N-dimethylaminopropyl (meth)acrylamide, and the like, as well as derivatives thereof.

Examples of specific polyfunctional acrylic monomers suitable for preparing polyacrylates (and polyacrylate moieties) include (alkyl)acrylic compounds having two or more acryloyl or methacryloyl groups, such as trimethylolpropane di(meth)acrylate, trimethylolpropane tri(meth)acrylate, polyoxyethylene-modified trimethylolpropane tri(meth) acrylate, polyoxypropylene-modified trimethylolpropane tri (meth)acrylate, polyoxyethylene/polyoxypropylene-modified trimethylolpropane tri(meth)acrylate, dimethyloltricyclodecane di(meth)acrylate, pentaerythritol tri(meth)acrylate, pentaerythritol tetra(meth)acrylate, ethylene glycol di(meth)acrylate, tetraethylene glycol di(meth) acrylate, phenylethylene glycol di(meth)acrylate, poly(ethylene glycol) di(meth)acrylate, poly(propylene glycol) di(meth)acrylate, 1,4-butanediol di(meth)acrylate, 1,6-hexanediol di(meth)acrylate, neopentyl glycol di(meth)acrylate, 1,9-nonanediol di(meth)acrylate, 1,10-decanediol di(meth)acrylate, 1,3-adamantanedimethanol di(meth)acrylate, o-xylylene di(meth)acrylate, m-xylylene di(meth)acrylate, p-xylylene di(meth)acrylate, tris(2-hydroxyethyl)isocyanurate tri(meth)acrylate, tris(acryloyloxy) isocyanurate, bis(hydroxymethyl)tricyclodecane di(meth)acrylate, dipentaerythritol penta(meth)acrylate, dipentaerythritol hexa(meth)acrylate, polyoxyethylene-modified 2,2-bis(4-((meth) acryloxy)phenyl)propane, polyoxypropylene-modified 2,2-bis(4-((meth)acryloxy)phenyl)propane, and polyoxyethylene/polyoxypropylene-modified 2,2-bis(4-((meth)acryloxy)phenyl)propane.

It is to be appreciated that the (alkyl)acrylic compounds above are described in terms of (meth)acrylate species only for brevity, and that one of skill in the art will readily understand that other alkyl and/or hydrido versions of such compounds may equally be utilized. For example, one of skill in the art will understand that the monomer "2-ethylhexyl (meth)acrylate" listed above exemplifies both 2-ethylhexyl (meth)acrylate as well as 2-ethylhexyl acrylate. Likewise, while the acrylic monomers are described generally as propenoates (i.e., α,β-unsaturated esters) in the examples above, it is to be appreciated that the that the term "acrylate" used in these descriptions may equally refer to an acid, salt, and/or conjugate base of the esters exemplified. For example, one of skill in the art will understand that the monomer "methyl acrylate" listed above exemplifies the methyl ester of acrylic acid, as well as acrylic acid, acrylate salts (e.g. sodium acrylate), etc. Furthermore, multifunctional derivatives/variations of the acrylic monomers described above may also be utilized. For example, the monomers "ethyl (meth)acrylate" listed above exemplifies functionalized-derivatives, such as substituted ethyl (meth) acrylates and ethyl acrylates (e.g. hydroxyethyl (meth) acrylate and hydroxyethyl acrylate, respectively).

Comonomers (i.e., monomers reactive with the acrylic monomers above) may also be utilized to prepare or otherwise present with the acrylate-functional compounds. Such monomers are not limited, and generally include compounds having a radically polymerizable group, such as an alkenyl, acryloyl, and alkylacryloyl groups. In general, comonomers are selected by one of skill the in art, e.g. to alter a property of the acrylate-functional compound and/or the copolymer formed therewith. For example, it is known in the art that styrene may be copolymerized with an acrylic monomer to prepare polyacrylates (and polyacrylate moieties) having increased hardness as compared to those absent such styrene comonomers. Likewise, comonomers such as acrylonitrile may be utilized to increase interchain polar interactions, and thus increase tensile strength and ultimate elongation of polyacrylates (and polyacrylate moieties), while also decreasing low temperature flexibility of such polyacrylates (and polyacrylate moieties). Moreover, one of skill in the art will readily selected the proportion(s) of monomers utilized, the order of addition, the length of reaction, and other factors to independently tune various properties (e.g. flexibility, solubility, hardness, polarity, etc.) of the polyacrylate moiety, the copolymer comprising the polyacrylate moiety, and/or compositions and/or products prepared therefrom. Specific examples of suitable comonomers include styrene, acrylonitrile, vinylidene chloride, vinyl chloride, ethylene, propylene, butylene, chloroprene, isoprene, tetrafluoroethylene, and the like, as well as derivatives thereof.

It is to be appreciated that combinations of acrylic monomers may also be utilized as or to prepare the acrylate-functional compound, such that the acrylate-functional compound may be homopolymeric or copolymeric with respect to any repeating segments therein. For example, the methods described above may be utilized to prepare multifunctional polyacrylates, e.g. by utilizing a monofunctional acrylic monomer and a polyfunctional acrylic monomer. These different functional monomers are typically selected by one of skill in the art, e.g. based on the reactivity and interpolymeric and/or intrapolymeric interactivity, to alter the mechanical strength of the polyacrylate prepared therewith. For example, cured products comprising the copolymer utilizing a polyacrylate moiety comprising a combination of monofunctional acrylic monomers and polyfunctional acrylic monomers can be prepared with increased mechanical strength as compared to those utilizing a homopolymeric polyacrylate moieties. Likewise, cured products comprising the copolymer utilizing a homopolymeric polyacrylate moiety may be prepared having increased flexibility as compared to those utilizing a polyfunctional polyacrylate moieties.

In specific embodiments, the acrylate-functional compound comprises or is prepared from methyl (meth)acrylate, methyl acrylate, butyl (meth)acrylate, butyl acrylate, 2-ethylhexyl (meth)acrylate, 2-ethylhexyl acrylate, hydroxyethyl (meth)acrylate, hydroxyethyl acrylate, methacrylic acid, acrylic acid, and/or styrene monomers.

It will also be appreciated that the acrylate-functional compound prepared as described above may be mono- or multifunctional with respect to the non-acrylic functional groups present therein. For example, such methods may be utilized to prepare polyacrylate alcohols, diols and/or polyols, including via the methods described above (e.g. by utilizing a hydroxyl-functional monomer) and modifications thereof (e.g. by utilizing a post-polymerization functionalization technique, such as endcapping and/or grafting a functional group-containing compound onto a polyacrylate. Such functional group-containing compounds include alkoxysilyl groups, e.g. which may be grafted onto a polyacrylate via hydrosilylation or other methods known in the art. For example, in certain embodiments, the polyacrylate moiety is prepared from a polyacrylate polyol. In these or other embodiments, the polyacrylate moiety is prepared from a polyacrylate compound comprising a dimethoxymethylsily group. In certain embodiments, the polyacrylate moiety is prepared from a polyacrylate compound comprising at least one radical polymerizable group, such as an acryloyl functional group.

The acrylate-functional compound typically has a number average molecular weight ($M_n$) of at least 100. In certain embodiments, the acrylate-functional compound has a $M_n$ of at least 100, alternatively at least 125, alternatively at least 150, alternatively at least 200, alternatively at least 250, alternatively at least 300. In these or other embodiments, each polyacrylate moiety has a $M_n$ of at least 200, alternatively at least 300, alternatively at least 400, alternatively at least 500, alternatively at least 600, alternatively at least 700, alternatively at least 1,000, alternatively at least 2,000, alternatively at least 4,000, alternatively at least 8,000. In certain embodiments, the acrylate-functional compound has a maximum $M_n$ of 100,000, alternatively less than 80,000, alternatively less than 60,000, alternatively less than 40,000, alternatively less than 20,000, alternatively less than 19,000, alternatively less than 18,000, alternatively less than 17,000, alternatively less than 16,000, alternatively less than 15,000. The number average molecular weight may be readily determined using Gel Permeation Chromatography (GPC) techniques based on polystyrene standards.

Carrier Vehicle

In certain embodiments, the composition further comprises a carrier vehicle. The carrier vehicle is not limited as is typically selected for polymerizing or reacting the branched organosilicon compound and the acrylate-functional compound therein. For example, the carrier vehicle of the composition is typically to prepare a copolymer from polymerizing or reacting the branched organosilicon compound and the acrylate-functional compound therein. However, the copolymer formed in the presence of the carrier vehicle can be removed from the carrier vehicle and disposed in an alternate vehicle or solvent for end use applications, e.g. via a solvent-exchange process. Said different, the carrier vehicle present in the composition may be different from any vehicle or solvent utilized in any end use application of the copolymer formed via this disclosure. Further still, the branched organosilicon compound and the acrylate-functional compound can be combined to give the composition neat, i.e., in the absence of the carrier vehicle.

In certain embodiments, the carrier vehicle comprises, alternative is, water. The water is not particularly limited, although the water is typically selected such that it is suitable for use in in cosmetic materials, quasi drugs, and pharmaceutical preparations. For example, purified water such as distilled water and ion exchanged water, saline, a phosphoric acid buffer aqueous solution, and the like can be used.

In other embodiments, the carrier vehicle may be, for example, an oil (e.g. an organic oil and/or a silicone oil), a solvent, etc.

In some embodiments, the carrier vehicle comprises, alternatively is, a silicone fluid. The silicone fluid is typically a low viscosity and/or volatile siloxane. In some embodiments, the silicone fluid is a low viscosity organopolysiloxane, a volatile methyl siloxane, a volatile ethyl siloxane, a volatile methyl ethyl siloxane, or the like, or combinations thereof. Typically, the silicone fluid has a viscosity at 25° C. in the range of 1 to 1,000 mm$^2$/sec. Specific examples of suitable silicone fluids include hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy}trisiloxane, hexamethyl-3,3, bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes, caprylyl methicone, hexamethyldisiloxane, heptamethyloctyltrisiloxane, hexyltrimethicone, and the like, as well as derivatives, modifications, and combinations thereof. Additional examples of suitable silicone fluids include polyorganosiloxanes with suitable vapor pressures, such as from $5 \times 10^{-7}$ to $1.5 \times 10^{-6}$ m$^2$/s, include DOWSIL® 200 Fluids and DOWSIL® OS FLUIDS, which are commercially available from Dow Silicones Corporation of Midland, Mich., U.S.A.

In certain embodiments, the carrier vehicle comprises, alternatively is, an organic fluid, which typically comprises an organic oil including a volatile and/or semi-volatile hydrocarbon, ester, and/or ether. General examples of such organic fluids include volatile hydrocarbon oils, such as $C_6$-$C_{16}$ alkanes, $C_8$-$C_{16}$ isoalkanes (e.g. isodecane, isododecane, isohexadecane, etc.) $C_8$-$C_{16}$ branched esters (e.g. isohexyl neopentanoate, isodecyl neopentanoate, etc.), and the like, as well as derivatives, modifications, and combinations thereof. Additional examples of suitable organic fluids include aromatic hydrocarbons, aliphatic hydrocarbons, alcohols having more than 3 carbon atoms, aldehydes, ketones, amines, esters, ethers, glycols, glycol ethers, alkyl halides, aromatic halides, and combinations thereof. Hydrocarbons include isododecane, isohexadecane, Isopar L ($C_{11}$-$C_{13}$), Isopar H ($C_{11}$-$C_{12}$), hydrogentated polydecene. Ethers and esters include isodecyl neopentanoate, neopentylglycol heptanoate, glycol distearate, dicaprylyl carbonate, diethylhexyl carbonate, propylene glycol n-butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, octyl ether, octyl palmitate, and combinations thereof.

In some embodiments, the carrier vehicle comprises, alternatively is, an organic solvent. Examples of the organic solvent include those comprising an alcohol, such as methanol, ethanol, isopropanol, butanol, and n-propanol; a ketone, such as acetone, methylethyl ketone, and methyl isobutyl ketone; an aromatic hydrocarbon, such as benzene, toluene, and xylene; an aliphatic hydrocarbon, such as heptane, hexane, and octane; a glycol ether, such as propylene glycol methyl ether, dipropylene glycol methyl ether, propylene glycol n-butyl ether, propylene glycol n-propyl ether, and ethylene glycol n-butyl ether; a halogenated hydrocarbon, such as dichloromethane, 1,1,1-trichloroethane and methylene chloride; chloroform; dimethyl sulfoxide; dimethyl formamide, acetonitrile; tetrahydrofuran; white spirits; mineral spirits; naphtha; n-methylpyrrolidone; and the like, as well as derivatives, modifications, and combination thereof.

Other carrier vehicles may also be utilized in the composition. For example, in some embodiments, the carrier vehicle comprises, alternatively is, an ionic liquid. Examples of ionic liquids include anion-cation combinations. Generally, the anion is selected from alkyl sulfate-based anions, tosylate anions, sulfonate-based anions, bis(trifluoromethanesulfonyl)imide anions, bis(fluorosulfonyl)imide anions, hexafluorophosphate anions, tetrafluoroborate anions, and the like, and the cation is selected from imidazolium-based cations, pyrrolidinium-based cations, pyridinium-based cations, lithium cation, and the like. However, combinations of multiple cations and anions may also be utilized. Specific examples of the ionic liquids typically include 1-butyl-1-methylpyrrolidinium bis(trifluoromethanesulfonyl)imide, 1-methyl-1-propylpyrrolidinium bis-(trifluoromethanesulfonyl)imide, 3-methyl-1-propylpyridinium bis(trifluoromethanesulfonyl)imide, N-butyl-3-methylpyridinium bis (trifluoromethanesulfonyl)imide, 1-methyl-1-propylpyridinium bis(trifluoromethanesulfonyl)imide, diallyldimethylammonium bis(trifluoromethanesulfonyl)imide, methyltrioctylammonium bis(trifluoromethanesulfonyl)imide, 1-butyl-3-methylimidazolium bis(trifluoromethanesulfonyl)imide, 1,2-dimethyl-3-propylimidazolium bis (trifluoromethanesulfonyl)imide, 1-ethyl-3-methylimidazolium bis(trifluoromethanesulfonyl)imide, 1-vinylimidazolium.bis(trifluoromethanesulfonyl)imide, 1-allyl imidazolium bis(trifluoromethanesulfonyl)imide, 1-allyl-3-methylimidazolium bis(trifluoromethanesulfonyl)imide, lithium bis(trifluoromethanesulfonyl)imide, and the like, as well as derivatives, modifications, and combinations thereof.

The carrier vehicle may comprise a combination of different vehicles, which may be miscible or immiscible with one another. For example, the composition itself may be homogenous or heterogeneous. The composition may also be in the form of an emulsion, such as a water-in-oil emulsion, silicone-in-oil emulsion, oil-in-water emulsion, oil-in-silicone emulsion, etc.

The amount of the carrier vehicle present in the composition depends on various factors. In general, where present, the composition comprises the carrier vehicle in an amount of from 1 to 99, alternatively from 1 to 75, alternatively from 2 to 60, alternatively from 2 to 50 wt. %, based on the total weight of the composition.

Inhibitor

In certain embodiments, the composition further comprises a polymerization inhibitor. The polymerization inhibitor is not limited, and may comprise, alternatively may be, a radical scavenger, an antioxidant, a light stabilizer, a UV-absorber, or the like, or a combination thereof. Such compounds are known in the art, and generally are, or include, a chemical compound or moiety capable of interacting with a free radical to render the free radical inactive, e.g. via elimination the free radical through the formation of a covalent bond therewith. The polymerization inhibitor may also, or alternatively, be a polymerization retardant, i.e., a compound that reduces the rate of initiation and/or propagation of a radical polymerization. For example, in some embodiments, the polymerization inhibitor comprises, alternatively is, oxygen gas. In general, the polymerization inhibitor is utilized to prevent and/or suppress the formation of byproducts that may be formed via radical polymerization of the branched organosilicon compound and acrylate-functional moiety.

The polymerization inhibitor is not limited, and may comprise, alternatively may be, a phenolic compound, a quinone or hydroquinone compound, an N-oxyl compound, a phenothiazine compound, a hindered amine compound, or a combination thereof.

Examples of phenolic compounds include phenol, alkylphenols, aminophenols (e.g. p-aminophenol), nitrosophenols, and alkoxyphenols. Specific examples of such phenol compounds include o-, m- and p-cresol(methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol, 2-methyl-4-tert-butylphenol, 4-tert-butyl-2,6-dimethylphenol or 2,2'-methylenebis(6-tert-butyl-4-methylphenol), 4,4'-oxybiphenyl, 3,4-methylenedioxydiphenol (sesamol), 3,4-dimethylphenol, pyrocatechol (1,2-dihydroxybenzene), 2-(1'-methylcyclohex-1'-yl)-4,6-dimethylphenol, 2- or 4-(1'-phenyleth-1'-yl)phenol, 2-tert-butyl-6-methylphenol, 2,4,6-tris-tert-butylphenol, 2,6-di-tert-butylphenol, nonylphenol, octylphenol, 2,6-dimethylphenol, bisphenol A, bisphenol B, bisphenol C, bisphenol F, bisphenol S, 3,3',5,5'-tetrabromobisphenol A, 2,6-di-tert-butyl-p-cresol, methyl 3,5-di-tert-butyl-4-hydroxybenzoate, 4-tert-butylpyrocatechol, 2-hydroxybenzyl alcohol, 2-methoxy-4-methylphenol, 2,3,6-trimethylphenol, 2,4,5-trimethylphenol, 2,4,6-trimethylphenol, 2-isopropylphenol, 4-isopropylphenol, 6-isopropyl-m-cresol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris-(3,5-di-tert-butyl-4-hydroxybenzyl)benzene, 1,3,5,-tris(3,5-di-tert-butyl-4-hydroxybenzyl)isocyanurate, 1,3,5-tris(3,5-di-tert-butyl-4-hydroxyphenyl)propionyloxyethyl isocyanurate, 1,3,5-tris(2,6-dimethyl-3-hydroxy-4-tert-butylbenzyl)isocyanurate or pentaerythrityl tetrakis[p-(3,5-di-tert-butyl-4-hydroxyphenyl)propionate], 2,6-di-tert-butyl-4-dimethylaminomethylphenol, 6-sec-butyl-2,4-dinitrophenol, octadecyl 3-(3',5'-di-tert-butyl-4'-hydroxyphenyl)propionate, hexadecyl 3-(3',5'-di-tert-butyl-4'-hydroxyphenyl)propionate, octyl 3-(3',5'-di-tert-butyl-4'-hydroxyphenyl)propionate, 3-thia-1,5-pentanediol bis[(3',5'-di-tert-butyl-4'-hydroxyphenyl)propionate], 4,8-dioxa-1,11-undecanediol bis[(3',5'-di-tert-butyl-4'-hydroxyphenyl)propionate], 4,8-dioxa-1,11-undecanediol bis[(3'-tert-butyl-4'-hydroxy-5'-methylphenyl)propionate], 1,9-nonanediol bis[(3',5'-di-tert-butyl-4'-hydroxyphenyl)propionate], 1,7-heptanediaminebis[3-(3',5'-di-tert-butyl-4'-hydroxyphenyl)propionamide], 1,1-methanediaminebis[3-(3',5'-di-tert-butyl-4'-hydroxyphenyl)propionamide], 3-(3',5'-di-tert-butyl-4'-hydroxyphenyl) propionic acid hydrazide, 3-(3',5'-dimethyl-4'-hydroxyphenyl)propionic acid hydrazide, bis(3-tert-butyl-5-ethyl-2-hydroxyphen-1-yl)methane, bis(3,5-di-tert-butyl-4-hydroxyphen-1-yl)methane, bis[3-(1'-methylcyclohex-1'-yl)-5-methyl-2-hydroxyphen-1-yl]methane, bis(3-tert-butyl-2-hydroxy-5-methylphen-1-yl)methane, 1,1-bis(5-tert-butyl-4-hydroxy-2-methylphen-1-yl)ethane, bis(5-tert-butyl-4-hydroxy-2-methylphen-1-yl) sulfide, bis(3-tert-butyl-2-hydroxy-5-methylphen-1-yl) sulfide, 1,1-bis(3,4-dimethyl-2-hydroxyphen-1-yl)-2-methylpropane, 1,1-bis(5-tert-butyl-3-methyl-2-hydroxyphen-1-yl)butane, 1,3,5-tris-[1'-(3Δ,5'''-di-tert-butyl-4'''-hydroxyphen-1'''-yl)meth-1'-yl]-2,4,6-trimethylbenzene, 1,1,4-tris(5'-tert-butyl-4'-hydroxy-2'-methylphen-1'-yl)butane and tert-butyleatechol, p-nitrosophenol, p-nitroso-o-cresol, methoxyphenol (guajacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol, 3,5-di-tert-butyl-4-hydroxyanisole, 3-hydroxy-4-methoxybenzyl alcohol, 2,5-dimethoxy-4-hydroxybenzyl alcohol (syringa alcohol), 4-hydroxy-3-methoxybenzaldehyde (vanillin), 4-hydroxy-3-ethoxybenzaldehyde (ethylvanillin), 3-hydroxy-4-methoxybenzaldehyde (isovanillin), 1-(4-hydroxy-3-methoxyphenyl)ethanone (acetovanillone), eugenol, dihydroeugenol, isoeugenol, tocopherols, such as α-, β-, γ-, δ- and ε-tocopherol, tocol, α-tocopherolhydroquinone, 2,3-dihydro-2,2-dimethyl-7-hydroxybenzofuran (2,2-dimethyl-7-hydroxycoumaran), and the like.

Suitable quinones and hydroquinones include hydroquinone, hydroquinone monomethyl ether(4-methoxyphenol), methylhydroquinone, 2,5-di-tert-butylhydroquinone, 2-methyl-p-hydroquinone, 2,3-dimethylhydroquinone, trimethylhydroquinone, 4-methylpyrocatechol, tert-butylhydroquinone, 3-methylpyrocatechol, benzoquinone, 2-methyl-p-hydroquinone, 2,3-dimethylhydroquinone, tdmethylhydroquinone, tert-butylhydroquinone, 4-ethoxyphenol, 4-butoxyphenol, hydroquinone monobenzyl ether, p-phenoxyphenol, 2-methylhydroquinone, tetramethyl-p-benzoquinone, diethyl-1,4-cyclohexanedion 2,5-dicarboxylate, phenyl-p-benzoquinone, 2,5-dimethyl-3-benzyl-p-benzoquinone, 2-isopropyl-5-methyl-p-benzoquinone (thymoquinone), 2,6-diisopropyl-p-benzoquinone, 2,5-dimethyl-3-hydroxy-p-benzoquinone, 2,5-dihydroxy-p-benzoquinone, embelin, tetrahydroxy-p-benzoquinone, 2,5-dimethoxy-1,4-benzoquinone, 2-amino-5-methyl-p-benzoquinone, 2,5-bisphenylamino-1,4-benzoquinone, 5,8-dihydroxy-1,4-naphthoquinone, 2-anilino-1,4-naphthoquinone, anthraquinone, N,N-dimethylindoaniline, N,N-diphenyl-p-benzoquinonediimine, 1,4-benzoquinone dioxime, coerulignone, 3,3'-di-tert-butyl-5,5'-dimethyldiphenoquinone, p-rosolic acid (aurin), 2,6-di-tert-butyl-4-benzylidenebenzoquinone, 2,5-di-tert-amylhydroquinone, and the like.

Suitable N-oxyl compounds (i.e., nitroxyl or N-oxyl radicals) include compounds which have at least one N—O• group, such as 4-hydroxy-2,2,6,6-tetramethylpiperidin-N-oxyl, 4-oxo-2,2,6,6-tetramethylpiperidin-N-oxyl, 4-methoxy-2,2,6,6-tetramethylpiperidin-N-oxyl, 4-acetoxy-2,2,6,6-tetramethylpiperidin-N-oxyl, 2,2,6,6-tetramethylpiperidin-N-oxyl (TEMPO), 4,4',4"-tris(2,2,6,6-tetramethylpiperidin-N-oxyl)phosphite, 3-oxo-2,2,5,5-tetramethylpyrrolidin-N-oxyl, 1-oxyl-2,2,6,6-tetramethyl-4-methoxypiperidine, 1-oxyl-2,2,6,6-tetramethyl-4-trimethylsilyloxypiperidine, 1-oxyl-2,2,6,6-tetramethylpiperidin-4-yl 2-ethylhexanoate, 1-oxyl-2,2,6,6-tetramethylpiperidin-4-yl sebacate, 1-oxyl-2,2,6,6-tetramethylpiperidin-4-yl stearate, 1-oxyl-2,2,6,6-tetramethylpiperidin-4-yl-benzoate, 1-oxyl-2,2,6,6-tetramethylpiperidin-4-yl (4-tert-butyl)benzoate, bis(1-oxyl-2,2,6,6-tetramethylpiperidin4-yl) succinate, bis(1-oxyl-2,2,6,6-tetramethylpiperidin-4-yl) adipate, bis(1-oxyl-2,2,6,6-tetramethylpiperidin-4-yl)1,10-decanedioate, bis(1-oxyl-2,2,6,6-tetramethylpiperidin4-yl)n-butylmalonate, bis(1-oxyl-2,2,6,6-tetramethylpiperidin-4-yl) phthalate, bis(1-oxyl-2,2,6,6-tetramethylpiperidin-4-yl)isophthalate, bis(1-oxyl-2,2,6,6-tetramethylpiperidin4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl)adipamide, N-(1-oxyl-2,2,6,6-tetramethylpiperidin-4-yl)caprolactam, N-(1-oxyl-2,2,6,6-tetramethylpiperidin-4-yl)dodecylsuccinimide, 2,4,6-tris[N-butyl-N-(1-oxyl-2,2,6,6-tetramethylpiperidin-4-yl]triazine, N,N'-bis(1-oxyl-2,2,6,6-tetramethylpiperidin-4-yl)-N,N'-bisformyl-1,6-diaminohexane, 4,4'-ethylenebis(1-oxyl-2,2,6,6-tetramethylpiperazin-3-one), and the like.

Other compounds suitable for use in or as the polymerization inhibitor include phenothiazine (PTZ) and compounds with similar structures, such as phenoxazine, promazine, N,N'-dimethylphenazine, carbazole, N-ethylcarbazole, N-benzylphenothiazine, N-(1-phenylethyl)phenothiazine, N-Alkylated phenothiazine derivatives such as N-benzylphenothiazine and N-(1-phenylethyl)phenothiazine, and the like. Of course, the polymerization inhibitor may include any number of particular compounds, which may each be independently selected and the same as or different from any other compound of the polymerization inhibitor.

When utilized, the polymerization inhibitor may be added to the composition as a discrete component, or may be combined with another component prior to the reaction of the branched organosilicon compound and the acrylate-functional compound. The polymerization inhibitor may be utilized in any amount, which will be selected by one of skill in the art, e.g. dependent upon the particular polymerization inhibitor selected, the reaction parameters employed, the scale of the reaction, the atmosphere of the reaction, the temperature and/or pressure of the reaction, etc.). In certain embodiments, the polymerization inhibitor is present in the reaction in an amount of from 50 to 2000 ppm, such as in an amount of 50, alternatively of 100, alternatively of 250, alternatively of 500, alternatively of 1000, alternatively of 1500, alternatively of 2000, ppm. However, one of skill in the art will readily appreciate that amounts outside of these ranges and exemplary amounts may also be utilized, e.g. where the reaction scale and/or conditions requires additional amounts of the polymerization inhibitor. Moreover, in addition or as an alternative to the above amounts, oxygen may be added to the reaction as a separate component (e.g. in place of, or in addition to, a discrete polymerization inhibitor selected from the compounds above). In such instances, the oxygen may be introduced into the reaction in the form of oxygen gas, optionally in the presence of other gasses (e.g. in the form of air). When utilized, the amount of oxygen gas is selected such that the gas phase above the reaction mixture remains below the explosion limit.

Initiator

In certain embodiments, the composition further comprises an initiator. The initiator is not limited and is typically a radical polymerization initiator that is conventionally used in polymerization of a vinyl-functional compound. Examples thereof include water-soluble peroxides, including inorganic peroxides such as potassium persulfate, sodium persulfate, and ammonium persulfate; and organic peroxides such as t-butylperoxy maleic acid, succinic acid peroxide, and t-butyl hydroperoxide. When an oil-soluble radical initiator is used, the oil-soluble radical initiator may be mixed with other components after the oil-soluble radical initiator is emulsified. The initiator is typically utilized in a range of from 0.01 to 20 parts by weight, alternatively from 0.1 to 10 parts by weight, based on 100 parts by weight total of component (A).

Surfactant

In certain embodiments, the composition further comprises a surfactant. When utilized, the surfactant is typically selected from an ionic surfactant (anionic surfactant, cationic surfactant, amphoteric surfactant, semipolar surfactant) and a nonionic surfactant. One type or a combination of two or more types of surfactants can be also used. Furthermore, a reactive surfactant having a radically polymerizable group can be also used.

Examples of anionic surfactants include saturated or unsaturated fatty acid salts (e.g. sodium laurate, sodium stearate, sodium oleate, sodium linolenate, and the like), alkylsulfuric acid salts, alkylbenzene sulfonic acids (e.g. hexylbenzenesulfonic acid, toctylbenzenesulfonic acid, dodecylbenzenesulfonic acid, and the like) and salts thereof, polyoxyalkylene alkyl ether sulfate salts, polyoxyalkylene alkenyl ether sulfate salts, polyoxyethylene alkylsulfate salts, alkyl sulfosuccinate salts, alkyl polyoxyalkylene sulfosuccinate salts, polyoxyalkylene alkylphenyl ether sulfate salts, alkane sulfonate salts, octyltrimethylammonium hydroxide, dodecyltrimethylammonium hydroxide, alkyl sulfonates, polyoxyethylene alkylphenyl ether sulfate salts, polyoxyalkylene alkyl ether acetate salts, alkyl phosphate salts, polyoxyalkylene alkyl ether phosphate salts, acylglutamate salts, α-acylsulfonate salts, alkylsulfonate salts, alkylallylsulfonate salts, α-olefin sulfonate salts, alkylnaphthalene sulfonate salts, alkane sulfonate salts, alkyl or alkenylsulfate salts, alkylamide sulfate salts, alkyl- or alkenyl phosphate salts, alkylamide phosphate salts, alkyloylalkyl taurinate salts, N-acylamino acid salts, sulfosuccinate salts, alkyl ether carboxylate salts, amide ether carboxylate salts, α-sulfofatty acid ester salts, alanine derivatives, glycine derivatives, arginine derivatives, and alkyl sulfoacetates.

In specific embodiments, an anionic surfactant formed from phosphoric acid, carboxylic acid, or amino acid is utilized, and examples thereof include alkyl ether carboxylates, unsaturated fatty acid salts (e.g. sodium laurate, sodium stearate, sodium oleate, sodium linoleate, and the like), octyltrimethylammonium hydroxide, dodecyltrimethylammonium hydroxide, polyoxyalkylene alkyl ether acetate salts, alkyl phosphate salts, polyoxyalkylene alkyl ether phosphate salts, acylglutamate salts, alkyl- or alkenyl phosphate salts, alkylamide phosphate salts, alkyloylalkyl taurinate salts, N-acyl amino acid salts, alkyl ether carboxylate salts, amide ether carboxylate salts, alanine derivatives, glycine derivatives, arginine derivatives, alkyl ether carboxylate salts, polyoxyalkylene alkyl ether carboxylate salts, alkyl phosphate salts, polyoxyalkylene alkyl ether phosphate salts, N-acyl amino acid salts, alkaline earth metal salts, magnesium salts, alkanolamine salts, triethanolamine salts, and ammonium salts. The counterion of the hydrophilic group of the anionic surfactant is typically $Na^+$, $K^+$, or $NH_4^+$.

Examples of nonionic surfactants include polyoxyalkylene ethers, polyoxyalkylene alkyl ethers, polyoxyalkylene fatty acid esters, polyoxyalkylene fatty acid diesters, polyoxyalkylene resinic acid esters, polyoxyalkylene (hydrogenated) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glyceric fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycols, diethylene glycol, polyoxyalkylene-modified silicones, polyglyceryl-modified silicones, glyceryl-modified silicones, saccharide-modified silicones, fluorine-based surfactants, polyoxyethylene-polyoxypropylene block polymers, and alkyl polyoxyethylene-polyoxypropylene block polymer ethers. In particular, polyoxyalkylene-modified silicones, polyglyceryl-modified silicones, glyceryl-modified silicones, and saccharide alcohol-modified silicones, which have an alkyl branch, linear-chain silicone branch, siloxane dendrimer branch, or the like, may be used simultaneously with the hydrophilic group.

Specific examples of cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium (2 EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, diethylaminoethylamide stearate, dimethylaminopropylamide stearate, behenic acid amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

Specific examples of the amphoteric surfactant include imidazoline-type, amidobetaine-type, alkylbetaine-type, alkylamidobetaine-type, alkylsulfobetaine-type, carbobetaine-type, phosphobetaine-type, aminocarboxylic acid-type, and amidoamino acid-type amphoteric surfactants, such as N-acylamidepropyl-N,N-dimethylammoniobetaines, N-acylamidepropyl-N,N'-dimethyl-N'-β-hydroxypropylammoniobetaines, and the like. Specific examples thereof include imidazoline-type amphoteric surfactants such as sodium 2-undecyl-N,N,N-(hydroxyethylcarboxymethyl)-2-imidazoline and disodium 2-cocoyl-2-imidazolinium hydroxide-1-carboxyethyloxy salt; alkylbetaine-type amphoteric surfactants such as lauryl dimethylaminoacetic betaine and myristyl betaine; amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric acid amidopropyl dimethylamino acetic acid betaine, myristic acid amidopropyl dimethylamino acetic acid betaine, palmitic acid amidopropyl dimethylamino acetic acid betaine, stearic acid amidopropyl dimethylamino acetic acid betaine, and oleic acid amidopropyl dimethylamino acetic acid betaine; phosphobetaine-type amphoteric surfactants such as hydroxy phosphobetaine; and amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine, and the like. Furthermore, the weight average molecular weight is typically 100 or greater.

Examples of semipolar surfactants include alkylamine oxide-type surfactants, alkylamine oxides, alkylamide amine oxides, alkylhydroxyamine oxides, and the like. Alkyldimethylamine oxides having from 10 to 18 carbons, alkoxyethyl dihydroxyethylamine oxides having from 8 to 18 carbons, and the like are typically used.

When utilized, the amount of the surfactant in the composition is typically from 0.1 to 30 parts by weight, and more typically from 0.1 to 10 parts by weight, per 100 parts by weight of component (A).

Catalyst

In various embodiments, the composition further comprises a catalyst. The catalyst can be used individually or as a combination of two or more in the composition. Examples of suitable catalyst include acids, such as carboxylic acids, e.g. formic acid, acetic acid, propionic acid, butyric acid, and/or valeric acid; bases, such as potassium hydroxyide; metal salts of organic acids, such as dibutyl tin dioctoate, iron stearate, and/or lead octoate; titanate esters, such as tetraisopropyl titanate and/or tetrabutyl titanate; chelate compounds, such as acetylacetonato titanium; aminopropyltriethoxysilane, and the like.

Optional Components

The composition may further comprise one or more various optional additives, such as coupling agents, antistatic agents, ultraviolet (UV) absorbers, plasticizers, leveling agents, preservatives, surface active materials (surfactants or detergents or emulsifiers), foam boosters, deposition agents, thickeners, water phase stabilizing agents, fillers, suspending agents, biocides, freeze/thaw additives, antifreeze agents, viscosity modifiers, foam control agents, dyestuff (e.g. pigments), binders and combinations thereof.

The composition can be a one component, two component, or multi-component composition. For example, the initiator, when present, may be separate from the branched organosilicon compound and the acrylate-functional compound so as to prevent premature reaction thereof.

In certain embodiments, a second siloxane is utilized along with the branched organosilicon compound when preparing the copolymer in the composition, as described above. As such, in certain embodiments, the composition can further comprise second siloxane different from the branched organosilicon compound. The second siloxane may be a dendric siloxane different from the branched organosilicon compound. Specific examples of second siloxanes include those having the following structures:

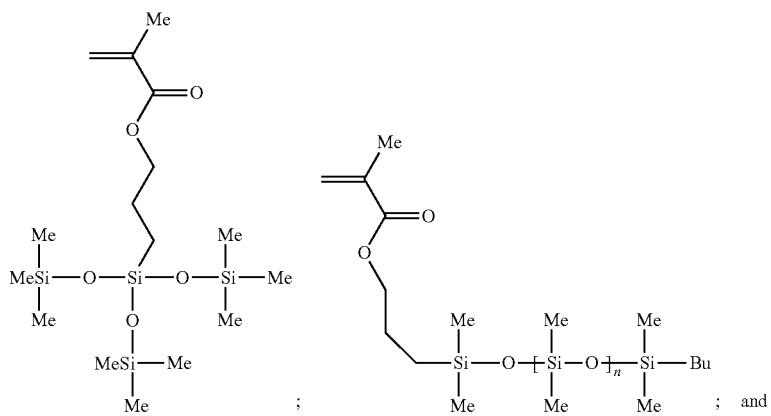

-continued

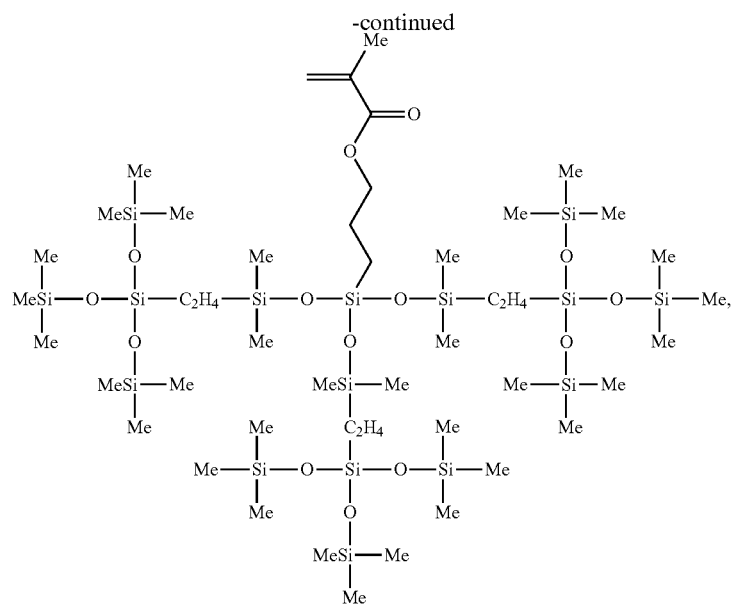

where Me is methyl and Bu is butyl.

Additional examples include methacryloxypropyltris(trimethylsiloxy)silane, α-butyldimethylsilyl- and ω-3-methacryloxypropyldimethylsilyl-terminated polydimethylsiloxane (CAS #149925-73-5), for example, MCR-M 07, MCR-M 11, MCR-M 17, MCR-M 22 from Gelest, and Silaplane FM 0711, Silaplane FM 0721, Silaplane FM 0725 from JNC. The second siloxane may be prepared in accordance with the disclosure of Example 1 of JP1999-001485.

Method

A method of preparing a copolymer is further provided. The method comprises reacting the branched organosilicon compound and the acrylate-functional compound in the presence of the carrier vehicle.

Generally speaking, the branched organosilicon compound and the acrylate-functional compound react in the presence of the initiator (and the carrier vehicle, as well as an optional components present in the composition). Thus, the method of preparing the copolymer generally requires contacting the branched organosilicon compound and the acrylate-functional compound in the presence of the initiator and the carrier vehicle.

There is no required order of addition of the components to form the composition or prepare the copolymer. For example, in one embodiment, the carrier vehicle comprises water. The branched organosilicon compound and the acrylate-functional compound can be dispersed or emulsified in the water acting as the carrier vehicle (e.g. the branched organosilicon compound and the acrylate-functional compound can be combined with water in any order, optional under shear or agitation). The initiator may be disposed in the composition or emulsion to initiate preparation of the copolymer from polymerizing or reacting the branched organosilicon compound and the acrylate-functional compound. Alternatively, in other embodiments, the branched organosilicon compound and the acrylate-functional compound can be mixed together neat to give a neat mixture, and the initiator may be disposed in the carrier fluid to give an initiator mixture. The neat mixture and the initiator mixture can be combined, optionally under agitation, to give the composition and prepare the copolymer by polymerizing or reacting the branched organosilicon compound and the acrylate-functional compound.

In certain embodiments, the method is carried out at an elevated temperature, i.e., the method comprises reacting the branched organosilicon compound and the acrylate-functional compound in the presence of the carrier vehicle at an elevate temperature. The elevated temperature typically accelerates the reaction between the branched organosilicon compound and the acrylate-functional compound. In certain embodiments, the elevated temperature is from greater than 25° C. up to a boiling temperature of the carrier vehicle; alternatively from 30 to 150, alternatively from 40 C to 120, alternatively from 50 to 110, alternatively from 60 to 100, alternatively from 70 to 70, ° C. Oxygen may optionally be removed from the composition during the method, e.g. by bubbling nitrogen or another inert gas into the composition.

The branched organosilicon compound and the acrylate-functional compound can be reacted at various molar ratios. In addition, the molar ratio of the branched organosilicon compound and the acrylate-functional compound is a function of the selection of the acrylate-functional compound (and branched organosilicon compound). The relative amounts of the acrylate-functional compound may differ when the acrylate-functional compound is a monomer versus a polymer. In certain embodiments, the branched organosilicon compound and the acrylate-functional compound are reacted in a molar ratio of from 1.5:1 to 1:1.5, alternatively from 1.4:1 to 1:1.4, alternatively from 1.3:1 to 1:1.3, alternatively from 1.2:1 to 1:1.2, alternatively from 1.1:1 to 1:1.1, alternatively from 1.1:1 to 1:1. However, one of skill in the art will select the particular ratios utilized, e.g. in view of the particular copolymer being prepared, the particular branched organosilicon compound and/or acrylate-functional compound being utilized, a desired use of the copolymer being prepared, the type of reaction being utilized in the polymerization method, etc.

The copolymer is the reaction product of the branched organosilicon compound and the acrylate-functional compound. As will be appreciated by one of skill in the art in view of the description herein, many variations or species of the copolymer may be prepared, e.g. depending on the particular branched organosilicon compound utilized, the particular acrylate-functional compound utilized, the type of reaction performed, the ratio of components utilized, etc.

In general, the copolymer comprises a branched organosilicon moiety having the formula:

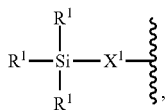

which is formed from the branched organosilicon compound utilized in the reaction with the reactive compound. As such, with regard to the branched organosilicon moiety of the copolymer, the organosilicon moiety represented by the subformula $R^1_3Si$— is as defined above with respect to the branched organosilicon compound. Subformula —$X^1$— is a moiety formed from the moiety X of the branched organosilicon compound (i.e., during the reaction of the branched organosilicon compound the acrylate-functional compound).

In some embodiments, the copolymer has the general formula:

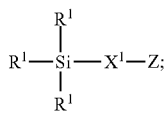

where the organosilicon moiety represented by the subformula $R^1_3Si$— is as defined above with respect to the branched organosilicon compound; —$X^1$— is a moiety formed from the moiety X of the branched organosilicon compound (i.e., during the reaction of the branched organosilicon compound the acrylate-functional compound); and Z is a polymer moiety formed from the acrylate-functional compound.

Moiety $X^1$ is formed from the moiety X of the branched organosilicon compound. As such, the particular nature (e.g. structure, formula, etc.) of $X^1$ will be controlled by the selection of the particular branched organosilicon compound and acrylate-functional compound to be utilized in preparing the copolymer, the type of reaction used therewith, etc., as will be understood by those of skill in the art in view of the description herein.

In certain embodiments, the copolymer has the general formula:

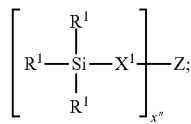

where moieties $R^1_3Si$—, —$X^1$—, and Z are as defined above, and subscript x" is ≥2. In such embodiments, the copolymer may comprise a linear structure, e.g. where subscript x" is 2, and the polymer moiety Z is linear, such that the copolymer has the general structure $R^1_3Si$—$X^1$—Z—$X^1$—Si—$R^1_3$. Alternatively, the copolymer may comprise a branched structure, such as where X is at least trivalent and subscript x" is ≥2, alternatively ≥3.

The copolymer is typically prepared in the presence of the carrier vehicle. Specific examples of the carrier vehicle are disclosed above. For example, the copolymer may be prepared in an aqueous carrier vehicle, or the copolymer may be prepared in an emulsion such that the carrier vehicle is other than water but the composition further comprises water.

Upon forming the copolymer, the copolymer may be dispersed in one or more types of oil agents, Examples of oil agents include animal oils, plant oils, synthetic oils, or the like that are generally used in cosmetics. As long as the oil agent is hydrophobic, the oil agent may be derived from any source, may be in the form of a solid, a semi-solid, or a liquid, and may be non-volatile, semi-volatile, or volatile. When the copolymer of the present invention is used in the form of the liquid composition, the oil agent may be a volatile liquid. Specific examples of suitable oil agents include silicone oils, hydrocarbon oils, and fatty acid ester oils. The oil agent may be the carrier vehicle or the copolymer may undergo an isolation or purification step, or a solvent exchange step, to be dispersed in the oil agent instead of the carrier vehicle.

The copolymer of the present invention has particularly excellent miscibility with the oil agent, and a copolymer composition may be obtained that is uniform over long durations. This composition may be used itself as a surface treatment agent without modification. Alternatively, this composition is extremely useful as a raw material for cosmetics. More particularly, a copolymer composition formed from 100 parts by mass of the copolymer of the present invention and from 5 to 1,000 parts by mass of the oil agent, alternatively from 50 to 500 parts by mass of the oil agent, alternatively from 100 to 400 parts by mass of the oil agent, may be used.

Suitable silicone oils are hydrophobic, and the molecular structure thereof may be a cyclic, linear, or branched structure. The viscosity of the silicone oils at 25° C. is usually in the range of from 0.65 to 100,000 mm²/s, alternatively from 0.65 to 10,000 mm²/s. Particularly, when the copolymer of the present invention is used as a cosmetic raw material, by inclusion of at least one type of such silicone oils, it is possible to improve time-wise stability of the obtained cosmetic, and it is possible to realize the characteristic fresh feel of a silicone oil.

Specific examples of the silicone oils include cyclic organopolysiloxanes, linear organopolysiloxanes, and branched organopolysiloxanes. Among these example silicone oils, volatile linear organopolysiloxanes, branched organopolysiloxanes, and cyclic organopolysiloxanes are most typical.

Specifically, examples of silicone oils include cyclic organopolysiloxanes such as hexamethyl cyclotrisiloxane (D3), octamethyl cyclotetrasiloxane (D4), decamethyl cyclopentasiloxane (D5), dodecamethyl-cyclohexasiloxane (D6), 1,1-diethylhexamethyl cyclotetrasiloxane, phenylheptamethyl cyclotetrasiloxane, 1,1-diphenylhexamethyl cyclotetrasiloxane, 1,3,5,7-tetravinyltetramethyl cyclotetrasiloxane, 1,3,5,7-tetramethyl cyclotetrasiloxane, 1,3,5,7-tetracyclohexyltetramethyl cyclotetrasiloxane, tris(3,3,3-trifluoropropyl) trimethylcyclotrisiloxane, 1,3,5,7-tetra(3-methacryloxypropyl) tetramethyl cyclotetrasiloxane, 1,3,5,7-tetra(3-acryloxypropyl) tetramethyl cyclotetrasiloxane, 1,3,5,7-tetra(3-carboxypropyl) tetramethyl cyclotetrasiloxane, 1,3,5,7-tetra(3-vinyloxypropyl) tetramethyl cyclotetrasiloxane, 1,3,5,7-tetra(p-vinylphenyl) tetramethyl cyclotetrasiloxane, 1,3,5,7-tetra[3-(p-vinylphenyl) propyl] tetramethyl cyclotetrasiloxane, 1,3,5,7-tetra(N-acryloyl-N- methyl-3-aminopropyl) tetramethyl cyclotetrasiloxane, 1,3, 5,7-tetra(N,N-bis(lauroyl)-3-aminopropyl) tetramethyl cyclotetrasiloxane, and the like.

Examples of straight organopolysiloxanes include dimethylpolysiloxane in which both molecular terminals are capped with trimethylsiloxy groups (dimethylsilicone with a low viscosity such as 2 cst or 6 cst to dimethylsilicone with a high viscosity such as 1,000,000 cst), organohydrogenpolysiloxane, methylphenylpolysiloxane in which both molecular terminals are capped with trimethylsiloxy groups, a copolymer of methylphenylsiloxane and dimethylsiloxane in which both molecular terminals are capped with trimethylsiloxy groups, diphenylpolysiloxane in which both molecular terminals are capped with trimethylsiloxy groups, a copolymer of diphenylsiloxane and dimethylsiloxane in which both molecular terminals are capped with trimethylsiloxy groups, trimethylpentaphenyltrisiloxane, phenyl (trimethylsiloxy) siloxane, methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl (3,3,3-trifluoropropyl) siloxane and dimethylsiloxane in which both molecular terminals are capped with trimethylsiloxy groups, α,ω-dihydroxypolydimethylsiloxane, α,ω-diethoxypolydimethylsiloxane, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyltrisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, a higher alkoxy-modified silicone, a higher fatty acid-modified silicone, and the like.

Examples of branched organopolysiloxanes include methyltristrimethylsiloxysilane, ethyltristrimethylsiloxysilane, propyltristrimethylsiloxysilane, tetrakistrimethylsiloxysilane, phenyltristrimethylsiloxysilane, or the like.

Typically, oil agents other than silicone oils are liquid at 5 to 100° C. As introduced above, suitable oil agents other than silicone oil are hydrocarbon oils and/or fatty ester oils. Such oil agents may be used alone or may be used together with the silicone oil.

When the copolymer of the present invention is used as a cosmetic raw material, by combined use of the hydrocarbon oil and/or fatty acid ester oil with the silicone oil, in addition to the characteristic fresh feel of the silicone oil, it is possible to retain the moisture on the skin and impart a smooth feel or moisture-retaining feel (also referred to as "moist feel") as if the skin or hair was wetted by the cosmetic. However, even when the copolymer of the present invention is used as a surface treatment agent, the copolymer of the present invention is advantageous in that time-wise stability of the cosmetic is not lost. Furthermore, with a cosmetic composition comprising the hydrocarbon oil and/or fatty acid ester oil and the silicone oil, these moisturizing components can be applied more stably and uniformly on the skin or hair, the moisturizing effects of the moisturizing component on the skin are improved and, compared to a cosmetic composition comprising only the oil agent other than the silicone oil (the hydrocarbon oil and/or fatty ester oil), a smoother, richer feeling to touch is imparted.

Examples of the hydrocarbon oil include liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene, and the like.

Examples of the fatty acid ester oil include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylolpropane tri-2-ethylhexanoate, ditrimethylolpropane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, 2-octyldodecyl N-lauroyl-L-glutamate, di(cholesteryl/behenyl/octyldodecyl) N-lauroyl-L-glutamate, di (cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, tridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca (erucate/isostearate/ricinoleate) (hexyldecanoic acid/sebacic acid) diglyceryl oligoester, glycol distearate (ethylene glycol distearate), diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensate, dimer dilinoleic acid hardened castor oil, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri (caprylate/caprate), glyceryl tri (caprylate/caprate/myristate/stearate), hydrogenated rosin triglyceride (hydrogenated ester gum), rosin triglyceride (ester gum), glyceryl behenate eicosane dioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of macadamia nut oil fatty acid, phytosteryl ester of macadamia nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain α-hydroxy fatty acid, octyldodecyl ricinoleate, octyldodecyl ester of lanolin fatty acid, octyldodecyl erucate, isostearic acid hardened castor oil, ethyl ester of avocado fatty acid, isopropyl ester of lanolin fatty acid, and the like.

In addition to the above, fats and oils, higher alcohols, higher fatty acids, fluorine-based oils, or the like may be used in combination of two or more types thereof. For example, the oil agents described below may also be used in combination of two or more types. Hereinafter, the oil agents other than silicone oils, hydrocarbon oils, and fatty acid ester oils that can be used in the present invention will be described in detail.

Examples of such fats and oils include natural animal or plant fats and oils and semi-synthetic fats and oils such as avocado oil, linseed oil, almond oil, ibota wax, *perilla* oil, olive oil, cacao butter, kapok wax, kaya oil, carnauba wax, liver oil, candelilla wax, beef tallow, neatsfoot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shea butter, Chinese tung oil, cinnamon oil, jojoba wax, olive squalane, shellac wax, turtle oil, soybean oil, tea seed oil, *camellia* oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, egg yolk oil, and the like. Herein, "POE" means "polyoxyethylene".

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerol ether (batyl alcohol), monooleyl glycerol ether (selachyl alcohol), and the like.

Examples of higher fatty acids include lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

Examples of the fluorine-based oil include perfluoropolyether, perfluorodecalin, perfluorooctane, and the like.

The copolymer has excellent film-forming ability. Films may be formed via wet coating application methods. Specific examples of wet coating application methods suitable for the method include dip coating, spin coating, flow coating, spray coating, roll coating, gravure coating, sputtering, slot coating, inkjet printing, and combinations thereof.

A composition is also provided. The composition includes the copolymer. The composition is generally without limitation, and can be of various forms, functions, uses, end applications, etc.

In various embodiments, the composition is further defined as at least one of: (i) an emulsion; (ii) an aqueous composition; (iii) a surfactant composition; (iv) a wetting composition; (v) an aqueous film-forming foam; (vi) a surface tension modifier; (vii) an antiblocking additive; (viii) an agricultural composition; (ix) a coating composition; (x) a paint composition; (xi) a surface treating composition; (xii) a film-forming composition; and (xiii) a cosmetic composition. One of skill in the art appreciates that certain compositions may overlap as to form and/or function. Reference to the composition and any one of these specific compositions, e.g. the emulsion, may be interchangeable in the description that follows.

The copolymer can also be used for numerous applications. In certain embodiments, the copolymer is used as at least one of a surface treating agent, an additive for paints, an additive for coatings, and a cosmetic ingredient.

The copolymer may react with—or be inert with respect to—other components present in the composition. In compositions or applications where the composition or copolymer contacts a surface or substrate, there may be bonding to the surface or substrate, with such bonding being mechanical/physical, chemical, or a combination thereof. For example, a surface may have functional groups that are reactive with the copolymer. Such functional groups may be inherent to the surface or may be imparted by one or more types of conventional surface treatment. Certain exemplary compositions and components thereof are described below.

It is to be appreciated that certain components or additives may be classified under different terms of art and just because a component or additive is classified under such a term does not mean that they are limited to that function. One or more of the additives can be present as any suitable weight percent (wt. %) of the composition, such as from 0.01 wt. % to 65 wt. %, alternatively from 0.05 wt. % to 35 wt. %, alternatively from 0.1 wt. % to 15 wt. %, alternatively from 0.5 wt. % to 5 wt. %, alternatively from 0.1 wt. % or less, based on the total weight of the composition. One of skill in the art can readily determine a suitable amount of additive depending, for example, on the type of additive and the desired outcome. Certain optional additives are described in greater detail below.

In various embodiments, the composition comprises or is an emulsion. The emulsion is without limitation, and is generally selected from the group of silicone/oil-in-water (O/W) and water-in-oil/silicone (W/O) emulsions. The emulsion comprises a non-aqueous phase and an aqueous phase. Typically, the non-aqueous phase is a discontinuous phase in the emulsion, and the aqueous phase is a continuous phase. However, the non-aqueous phase may be the continuous phase, with the aqueous phase being the discontinuous phase, based on the relevant amounts of components therein, as described below.

The discontinuous phase generally forms particles in the continuous phase of the emulsion. The particles are liquid and may alternatively be referred to as droplets. The size of the particles is typically contingent on, for example, the selection of components therein and their amounts.

In various embodiments, the non-aqueous phase of the emulsion comprises the copolymer of this disclosure. In certain embodiments, the non-aqueous phase further comprises a carrier vehicle for the copolymer. The carrier vehicle may be selected from vehicles understood in the art, such as siloxane carrier vehicles, inorganic and organic solvents, etc. In other or further embodiments, the non-aqueous phase further comprises a surfactant, as described further below.

Exemplary emulsions, compositions comprising emulsions, and films formed therewith, are described in WO2018145069A1.

Representative non-limiting examples of organic solvents include toluene, xylene, and similar aromatic hydrocarbons; hexane, heptane, isooctane, and similar linear or partially branched saturated hydrocarbons; cyclohexane and similar aliphatic hydrocarbons; low molecular weight alcohols such as methanol, ethanol, propanol, isopropanol and the like; low molecular weight ethers such as di(propyleneglycol) mono methyl ether, di(ethyleneglycol) butyl ether, di(ethyleneglycol) methyl ether, di(propyleneglycol) butyl ether, di(propyleneglycol) methyl ether acetate, di(propyleneglycol) propyl ether, ethylene glycol phenyl ether, propylene glycol butyl ether, 1-methoxy-2-propanol, 1-methoxy-2-propyl acetate, propylene glycol propyl ether, 1-phenoxy-2-propanol, tri(propyleneglycol) methyl ether and tri(propyleneglycol) butyl ether, and other like glycols.

The aqueous phase comprises water. The water may be from any source and may optionally be purified, e.g. through filtration, distillation, reverse-osmosis techniques, etc.

In many embodiments, the emulsion further comprises a surfactant. The surfactant may alternatively be referred to as an emulsifier and generally serves to emulsify the non-aqueous phase in the aqueous phase of the emulsion. The surfactant may be any surfactant suitable for preparing the emulsion with the non-aqueous phase and the aqueous phase.

For example, the surfactant may comprise one or more anionic, cationic, nonionic, and/or amphoteric surfactants, organomodified silicones such as dimethicone copolyol, oxyethylenated and/or oxypropylenated ethers of glycerol, oxyethylenated and/or oxypropylenated ethers of fatty alcohols such as ceteareth-30, C12-15 pareth-7, fatty acid esters of polyethylene glycol such as PEG-50 stearate, PEG-40 monostearate, saccharide esters and ethers such as sucrose stearate, sucrose cocoate and sorbitan stearate, and mixtures thereof, phosphoric esters and salts thereof such as DEA oleth-10 phosphate, sulphosuccinates such as disodium PEG-5 citrate lauryl sulphosuccinate and disodium ricinoleamido MEA sulphosuccinate, alkyl ether sulphates such as sodium lauryl ether sulphate, isethionates, betaine derivatives, and mixtures thereof.

In certain embodiments, the surfactant comprises the anionic surfactant. Anionic surfactants include, for example, carboxylates (sodium 2-(2-hydroxyalkyloxy)acetate)), amino acid derivatives (N-acylglutamates, N-acylglycinates or acylsarcosinates), alkyl sulfates, alkyl ether sulfates and oxyethylenated derivatives thereof, sulfonates, isethionates and N-acylisethionates, taurates and N-acyl N-methyltaurates, sulfosuccinates, alkylsulfoacetates, phosphates and alkyl phosphates, polypeptides, anionic derivatives of alkyl polyglycoside (acyl-D-galactoside uronate), and fatty acid soaps, alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate and triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid, and mixtures thereof.

In these or other embodiments, the surfactant comprises the cationic surfactant. Cationic surfactants include, for example, various fatty acid amines and amides and their derivatives, and the salts of the fatty acid amines and amides. Examples of aliphatic fatty acid amines include dodecylamine acetate, octadecylamine acetate, and acetates of the amines of tallow fatty acids, homologues of aromatic amines having fatty acids such as dodecylanalin, fatty amides derived from aliphatic diamines such as undecylimidazoline, fatty amides derived from aliphatic diamines such as asundecylimidazoline, fatty amides derived from disubstituted amines such as oleylaminodiethylamine, derivatives of ethylene diamine, quaternary ammonium compounds and their salts which are exemplified by tallow trimethyl ammonium chloride, dioctadecyldimethyl ammonium chloride, didodecyldimethyl ammonium chloride, dihexadecyl ammonium chloride, alkyltrimethylammonium hydroxides such as octyltrimethylammonium hydroxide, dodecyltrimethylammonium hydroxide, and hexadecyltrimethylammonium hydroxide, dialkyldimethylammonium hydroxides such as octyldimethylammonium hydroxide, decyldimethylammonium hydroxide, didodecyldimethylammonium hydroxide, dioctadecyldimethylammonium hydroxide, tallow trimethylammonium hydroxide, coconut oil, trimethylammonium hydroxide, methylpolyoxyethylene cocoammonium chloride, and dipalmitylhydroxyethylammonium methosulfate, amide derivatives of amino alcohols such as beta-hydroxylethylstearylamide, amine salts of long chain fatty acids, and mixtures thereof.

In these or other embodiments, the surfactant comprises the nonionic surfactant. Nonionic surfactants include, for example, polyoxyethylene alkyl ethers (such as, lauryl, cetyl, stearyl or octyl), polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, polyoxyalkylene glycol modified polysiloxane surfactants, polyoxyalkylene-substituted silicones (rake or ABn types), silicone alkanolamides, silicone esters, silicone glycosides, dimethicone copolyols, fatty acid esters of polyols, for instance sorbitol and glyceryl mono-, di-, tri- and sesquioleates and stearates, glyceryl and polyethylene glycol laurates; fatty acid esters of polyethylene glycol (such as polyethylene glycol monostearates and monolaurates), polyoxyethylenated fatty acid esters (such as stearates and oleates) of sorbitol, and mixtures thereof.

In these or other embodiments, the surfactant comprises the amophoteric surfactant. Amphoteric surfactants, include, for example, amino acid surfactants, betaine acid surfactants, trimethylnonyl polyethylene glycol ethers and polyethylene glycol ether alcohols containing linear alkyl groups having from 11 to 15 carbon atoms, such as 2,6,8-trimethyl- 4-nonyloxypolyethylene oxyethanol (6 EO) (sold as Tergitol® TMN-6 by OSi Specialties, A Witco Company, Endicott, NY), 2,6,8-trimethyl-4-nonyloxypolyethylene oxyethanol (10 EO) (sold as Tergitol® TMN-10 by OSi Specialties, A Witco Company, Endicott, NY), alkylene-oxypolyethylene oxyethanol ($C_{11-15}$ secondary alkyl, 9 EO) (sold as Tergitol® 15-S-9 by OSi Specialties, A Witco Company, Endicott, NY), alkylene-oxypolyethylene oxyethanol ($C_{11-15}$ secondary alkyl, 15 EO) (sold as Tergitol® 15-S-15 by OSi Specialties, A Witco Company, Endicott, NY), octylphenoxy polyethoxy ethanols having varying amounts of ethylene oxide units such as octylphenoxy polyethoxy ethanol (40 EO) (sold as Triton® X405 by Rohm and Haas Company, Philadelphia, Pa.), nonionic ethoxylated tridecyl ethers available from Emery Industries, Mauldin, S.C. under the general tradename Trycol, alkali metal salts of dialkyl sulfosuccinates available from American Cyanamid Company, Wayne, N.J. under the general tradename Aerosol, polyethoxylated quaternary ammonium salts and ethylene oxide condensation products of the primary fatty amines (available from Armak Company, Chicago, Illinois under the tradenames Ethoquad, Ethomeen, or Arquad), polyoxyalkylene glycol modified polysiloxanes, N-alkylamidobetaines and derivatives thereof, proteins and derivatives thereof, glycine derivatives, sultaines, alkyl polyaminocarboxylates and alkylamphoacetates, and mixtures thereof. These surfactants may also be obtained from other suppliers under different tradenames.

The surfactant may be included in the emulsion at concentrations effective for emulsifying the non-aqueous phase in the aqueous phase (or vice versa). Such concentrations range from greater than 0 to 10, alternatively from 0.3 to 5, weight percent based on the total weight of the emulsion. The surfactant, or combination of surfactants, may be present in the aqueous phase of the emulsion, the non-aqueous phase of the emulsion, an interface of the aqueous and non-aqueous phases, or combinations thereof.

The emulsion may further comprise one or more various optional additives, such as coupling agents, antistatic agents, ultraviolet (UV) absorbers, plasticizers, leveling agents, preservatives, surface active materials (surfactants or detergents or emulsifiers), foam boosters, deposition agents, thickeners, water phase stabilizing agents, fillers, suspending agents, biocides, freeze/thaw additives, anti-freeze agents, viscosity modifiers, foam control agents, dyestuff (e.g. pigments), binders and combinations thereof.

Alternatively or in addition to the above, the emulsion may further comprise various additive compounds for improving properties of the film formed therefrom. Examples of additive compounds are silanes, such as tetrakis(dimethylamine)silane, tetraethylorthosilicate, glycidoxypropyltrimethoxysilane, triethylsilane, isobutyltrimethoxysilane; and siloxanes, such as heptamethyltrisiloxane, tetramethyldisiloxane, etc.

In some embodiments, the emulsion is a coating composition, or may be formulated into a coating composition. Such coating compositions are typically utilized to provide a continuous protective coating on a substrate by applying the coating composition to a surface of the substrate. Examples of such substrates include organic or inorganic components, and may include household materials such as leathers, papers, woods, metals, plastics, fabrics, paints, and the like. The coating compositions may also be suitable for use in other applications as well, e.g. as a protective and/or decorative coating, as a component in a paint, etc.

In various embodiments, the copolymer can be used as additives for epoxy coatings. Numerous epoxy coatings are understood in the art, including those described in U.S. Pat. No. 8,722,148 and US20060205861.

In various embodiments, the composition comprises the emulsion and an organic binder. The emulsion can be formed in situ in the composition, or the emulsion can be first prepared and then combined with the organic binder, along with any other optional components, to give the composition. In certain embodiments, the composition is formed by combining the emulsion and the organic binder, along with any optional components. The emulsion typically is present in the composition, i.e., forming the composition with the emulsion doesn't destroy the emulsion.

The organic binder is not limited and is generally selected based on end use applications of the composition. While exemplary examples are set forth below, any organic binder may be utilized in the composition. The organic binder may be reactive or non-reactive, and may be a thermoplastic and/or thermoset. Typically, the organic binder is an organic polymer and/or resin.

In certain embodiments, the organic binder comprises a natural latex. In these or other embodiments, the organic binder comprises a synthetic latex. The organic binder may also be a combination of natural and synthetic latex. For example, the organic binder is typically a natural and/or synthetic latex when the composition is utilized to prepare films or paints. Natural and synthetic latexes are known in the art. For example, depending on a selection of the organic binder, the composition may be utilized as a paint, e.g. a heat resistant paint, which may be solventless. The paint may be utilized in insulation applications, anti-fouling applications, architectural applications, commercial/industrial or residential applications, protective applications, leather applications, textile applications, etc.

Specific examples of organic binders include, but are not limited to, polyolefins, acrylic polymers, polyvinyl acetate, polyvinyl chloride, styrenes (e.g. styrene-butadiene rubber), acrylonitrile-butadienes, epoxy resins, phenolics, polyesters, polyvinylbutyral, phenoxys, polyureas, cellulosic resins, polyurethanes, polyamides, polyethers, alkyds, silicones, acrylonitriles, etc. The organic binder may comprise a combination of such organic binders, or copolymers or terpolymers including one or more such organic binders.

The content of the organic binder in the composition may vary on a number of factors, such as its selection, the type and amount of the emulsion present in the composition, end use applications of the composition, etc. Increased loadings of the organic binder generally result in films having greater hardness and other increased physical properties. In certain embodiments, the composition comprises the binder in an amount of from greater than 0 to less than 100, alternatively from greater than 0 to 50, alternatively from 0.1 to 40, alternatively from 5 to 15, wt. % based on the total weight of the composition.

The organic binder may be dispersed or disposed in a carrier vehicle. The carrier vehicle may be any suitable carrier vehicle, which typically solubilizes the organic binder. The carrier vehicle is typically a function of the organic binder utilized. The carrier vehicle may be water such that the composition as a whole is water-based, or may be a solvent other than water, e.g. an organic solvent. In certain embodiments, like the emulsion, the composition is substantially free from water. Substantially free from water is defined with respect to the emulsion.

In some embodiments the composition further comprises one or more optional components. The composition may comprise any of the optional components described above with respect to the emulsion. These optional components may be included in the composition from being present in the emulsion, may be incorporated into the composition independent from the emulsion, or both. Specific examples of optional components include, but are not limited to, colorants, coalescing aids, surfactants, thickeners, defoamers, compatibilizers, UV stabilizers, antioxidants, biocides, flame retardants, etc., Some of these optional components may be present in the emulsion, as described above, and thus included in the composition, or one or more of these optional components may be incorporated when forming the composition. Any of the optional components described above relative to the emulsion may also be present in the composition, either through introduction from the emulsion or from inclusion of an additional amount of the particular component. By way of example, the composition may comprise a catalyst, which may be the same as or different from any catalyst that may be present in the emulsion.

In certain embodiments, the composition further comprises one or more colorants, such as pigments, dyes, and the like. Such colorants can be organic or inorganic, synthetic or natural. Examples of colorants are set forth above regarding the emulsion. The emulsion and the composition itself may include different colorants which are independently selected. Additional examples of suitable colorants include cadmium yellow, cadmium red, cadmium green, cadmium orange, carbon black (including vine black, lamp black), ivory black (bone char), chrome yellow, chrome green, cobalt violet, cobalt blue, cerulean blue, aureolin (cobalt yellow), Azurite, Han purple, Han blue, Egyptian blue, Malachite, Paris green, Phthalocyanine Blue BN, Phthalocyanine Green G, verdigris, viridian, sanguine, caput mortuum, oxide red, red ochre, Venetian red, Prussian blue, yellow ochre, raw sienna, burnt sienna, raw umber, burnt umber, Cremnitz white, Naples yellow, vermilion titanium yellow, titanium beige, titanium white ($TiO_2$), titanium black, ultramarine, ultramarine green shade, zinc white, zinc ferrite, alizarin (synthesized or natural), alizarin crimson (synthesized or natural), gamboge, cochineal red, rose madder, indigo, Indian yellow, Tyrian purple, quinacridone, magenta, phthalo green, phthalo blue, pigment red 170, or any combinations thereof.

In particular embodiments, the composition further comprises a coalescing aid. Suitable coalescing aids include any compound that decreases the minimum film-formation temperature of the organic binder, when the organic binder indeed forms a film, and/or increases the rate of solid film formation from the organic binder when any carrier vehicle or water is removed from the composition. Examples of suitable coalescing aids include glycol ethers, 2,2,4-trimethyl-1,3-pentanediol isobutyrate, and combinations thereof In certain embodiments, the composition comprises a surfactant. The surfactant may be the same as or different from any surfactant utilized in the emulsion, examples of which are set forth above.

Thickeners (or rheology modifiers) may also be included in the composition to achieve desired viscosity and flow properties. Depending on their selection, as the selection of the organic binder, the thickeners may function by, for example, forming multiple hydrogen bonds with the organic binder, thereby causing chain entanglement, looping and/or swelling which results in volume restriction. In certain embodiments, thickeners such as cellulose derivatives including hydroxyethyl cellulose, methyl cellulose and carboxymethyl cellulose, may be utilized.

In some embodiments, the composition includes a defoamer. The defoamer may be any suitable chemical additive that reduces and hinders the formation of foam in the composition. Defoamers are known in the art and are typically selected based on other components present in the composition.

When the composition comprises the compatibilizer, the compatibilizer may be any compound or component which modifies, alternatively improves, the wetting of the components in the composition. Examples of such compatibilizers include titanium alcoholates, esters of phosphoric, phosphorous, phosphonic, and silicic acids, metallic salts and esters of aliphatic, aromatic, and cycloaliphatic acids, ethylene/acrylic or methacrylic acids, ethylene/esters of acrylic or methacrylic acid, ethylene/vinyl acetate resins, styrene/maleic anhydride resins or esters thereof, acrylonitrilebutadiene styrene resins, methacrylate/butadiene styrene resins (MBS), styrene acrylonitrile resins (SAN), and butadieneacrylonitrile copolymers. Alternatively or in addition, the compatibilizer may comprise a silane, e.g. a hydrocarbonoxysilane such as an alkoxysilane, a combination of an alkoxysilane and a hydroxy-functional polyorganosiloxane, an aminofunctional silane, or a combination thereof. The silane may include any functional group, which may be an adhesion-promoting group, such as amino, epoxy, mercapto and/or acrylate groups. Combinations of functional groups may be utilized, e.g. the (D) compatibilizer may comprise an epoxy-functional alkoxysilane. Suitable epoxy-functional organic groups are exemplified by 3-glycidoxypropyl and (epoxycyclohexyl)ethyl. Unsaturated organic groups are exemplified by 3-methacryloyloxypropyl, 3-acryloyloxypropyl, and unsaturated monovalent hydrocarbon groups such as vinyl, allyl, hexenyl, undecylenyl. Examples of suitable epoxy-functional alkoxysilanes include 3-glycidoxypropyltrim ethoxysilane, 3-glycidoxypropyltriethoxysilane, (epoxycyclohexyl)ethyldimethoxysilane, (epoxycyclohexyl)ethyldiethoxysilane and combinations thereof. Examples of suitable unsaturated alkoxysilanes include vinyltrimethoxysilane, allyltrimethoxysilane, allyltriethoxysilane, hexenyltrimethoxysilane, undecylenyltrimethoxysilane, 3-methacryloyloxypropyl trimethoxysilane, 3-methacryloyloxypropyl triethoxysilane, 3-acryloyloxypropyl trimethoxysilane, 3-acryloyloxypropyl triethoxysilane, and combinations thereof. Aminofunctional silanes, such as an aminofunctional alkoxysilanes, may have various amino groups, as understood in the art. Other examples of compatibilizers include modified polyethylene and modified polypropylene, which are obtained by modifying polyethylene and polypropylene, respectively, using a reactive group, including polar monomers such as maleic anhydride or esters, acrylic or methacrylic acid or esters, vinylacetate, acrylonitrile, and styrene.

Specific examples of UV stabilizers include phenol, 2-(2H-benzotriazol-2-yl)-6-dodecyl-4-methyl-, branched and linear (TINUVIN® 571). Additional examples of suitable UV stabilizers include bis(1,2,2,6,6-pentamethyl-4-piperidyl) sebacate; methyl 1,2,2,6,6-pentamethyl-4-piperidyl/sebacate; and a combination thereof (TINUVIN® 272). These and other TINUVIN® additives, such as TINUVIN® 765 are commercially available from Ciba Specialty Chemicals of Tarrytown, N.Y., U.S.A. Other UV and light stabilizers are commercially available, and are exemplified by LowLite from Chemtura, OnCap from PolyOne, and Light Stabilizer 210 from E. I. du Pont de Nemours and Company of Delaware, U.S.A. An example of an oligomeric antioxidant stabilizer (specifically, hindered amine light stabilizer (HALS)) is Ciba TINUVIN® 622, which is a dimethylester of butanedioic acid copolymerized with 4-hydroxy-2,2,6,6-tetramethyl-1-piperidine ethanol.

If utilized, the antioxidant may be any antioxidant known in the art. Specific examples thereof include phenolic antioxidants and combinations of phenolic antioxidants with stabilizers. Phenolic antioxidants include fully sterically hindered phenols and partially hindered phenols; and sterically hindered amines such as tetramethyl-piperidine derivatives. Suitable phenolic antioxidants include vitamin E and IRGANOX® 1010 from Ciba Specialty Chemicals, U.S.A. IRGANOX® 1010 comprises pentaerythritol tetrakis(3-(3,5-di-t-butyl-4-hydroxyphenyl)propionate). Additional examples of antioxidants are acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, Camellia sinensis oil, chitosan ascorbate, chitosan glycolate, chitosan salicylate, chlorogenic acids, cysteine, cysteine HCl, decyl mercaptomethylimidazole, erythorbic acid, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (Melaleuca aftemifolia) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, zinc dibutyldithiocarbamate, and mixtures thereof.

Biocides may be exemplified by fungicides, herbicides, pesticides, antimicrobial agents, or a combination thereof.

Specific examples of fungicides include N-substituted benzimidazole carbamate, benzimidazolyl carbamate such as methyl 2-benzimidazolylcarbamate, ethyl 2-benzimidazolylcarbamate, isopropyl 2-benzimidazolylcarbamate, methyl N-{2-[I-(N,N-dimethylcarbamoyl)benzimidazolyl]}carbamate, methyl N-{2-[1-(N,N-dimethylcarbamoyl)-6-methylbenzimidazolyl]}carbamate, methyl N-{2-[1-(N,N-dimethylcarbamoyl)-5-methylbenzimidazolyl]}carbamate, methyl N-{2-[I-(N-methylcarbamoyl)benzimidazolyl]}carbamate, methyl N-{2-[I-(N-methylcarbamoyl)-6-methylbenzimidazolyl]}carbamate, methyl N-{2-[I-(N-methylcarbamoyl)-5-methylbenzimidazolyl]}carbamate, ethyl N-{2-[I-(N,N-dimethylcarbamoyl)benzimidazolyl]}carbamate, ethyl N-{2-[2-(N-methylcarbamoyl)benzimidazolyl]}carbamate, ethyl N-{2-[1-(N,N-dimethylcarbamoyl)-6-methylbenzimidazolyl]}carbamate, ethyl N-{2-[I-(N-methylcarbamoyl)-6-methylbenzimidazolyl]}carbamate, isopropyl N-{2-[I-(N,N-dimethylcarbamoyl)benzimidazolyl]}carbamate, isopropyl N-{2-[I-(N-methylcarbamoyl)benzimidazolyl]}carbamate, methyl N-{2-[I-(N-propylcarbamoyl) benzimidazolyl]}carbamate, methyl N-{2-[I-(N-butylcarbamoyl)benzimidazolyl]}carbamate, methoxyethyl N-{2-[I-(N-propylcarbamoyl)benzimidazolyl]}carbamate, methoxyethyl N-{2-[I-(N-butylcarbamoyl)benzimidazolyl]} carbamate, ethoxyethyl N-{2-[I-(N-propylcarbamoyl)benzimidazolyl]}carbamate, ethoxyethyl N-{2-[I-(N-butylcarbamoyl)benzimidazolyl]}carbamate, methyl N-{1-(N,N-dimethylcarbamoyloxy)benzimidazolyl]}carbamate, methyl N-{2-[N-methylcarbamoyloxy)benzimidazolyl]}carbamate, methyl N-{2-[I-(N-butylcarbamoyloxy)benzoimidazolyl]}carbamate, ethoxyethyl N-{2-[I-(N-propylcarbamoyl)benzimidazolyl]}carbamate, ethoxyethyl N-{2-[I-(N-butylcarbamoyloxy)benzoimidazolyl]}carbamate, methyl N-{2-[I-(N,N-dimethylcarbamoyl)-6-chlorobenzimidazolyl]}carbamate, and methyl N-{2-[I-(N,N-dimethylcarbamoyl)-6-nitrobenzimidazolyl]}carbamate; 10,10'-oxybisphenoxarsine (which has trade name Vinyzene, OB PA), di-iodomethyl-para-tolylsulfone, benzothiophene-2-cyclohexylcarboxamide-S,S-dioxide, N-(fluordichloridemethylthio)phthalimide (which has trade names Fluor-Folper, and Preventol A3); methyl-benzimideazol-2-ylcarbamate (which has trade names Carbendazim, and Preventol BCM), zinc-bis(2-pyridylthio-I-oxide) (zinc pyrithion) 2-(4-thiazolyl)-benzimidazol, N-phenyl-iodpropargylcarbamate, N-octyl-4-isothiazolin-3-on, 4,5-dichloride-2-n-octyl-4-isothiazolin-3-on, N-butyl-1,2-benzisothiazolin-3-on and/or triazolyl-compounds, such as tebuconazol in combination with zeolites containing silver.

Alternatively, the biocide may comprise a boron containing material, e.g., boric anhydride, borax, or disodium octaborate tetrahydrate; which may function as a pesticide, fungicide, and/or flame retardant.

Specific examples of suitable flame retardants include carbon black, hydrated aluminum hydroxide, and silicates such as wollastonite, platinum and platinum compounds. Alternatively, the flame retardant, if utilized, may be selected from halogen based flame-retardants such as decabromodiphenyloxide, octabromodiphenyl oxide, hexabromocyclododecane, decabromobiphenyl oxide, diphenyoxybenzene, ethylene bis-tetrabromophthalmide, pentabromoethyl benzene, pentabromobenzyl acrylate, tribromophenyl maleic imide, tetrabromobisphenyl A, bis-(tribromophenoxy) ethane, bis-(pentabromophenoxy) ethane, polydibromophenylene oxide, tribromophenylallyl ether, bis-dibromopropyl ether, tetrabromophthalic anhydride, dibromoneopentyl gycol, dibromoethyl dibromocyclohexane, pentabromodiphenyl oxide, tribromostyrene, pentabromochlorocyclohexane, tetrabromoxylene, hexabromocyclododecane, brominated polystyrene, tetradecabromodiphenoxybenzene, trifluoropropene and PVC. Alternatively, the flame retardant, if utilized, may be selected from phosphorus based flame-retardants such as (2,3-dibromopropyl)-phosphate, phosphorus, cyclic phosphates, triaryl phosphate, bis-melaminium pentate, pentaerythritol bicyclic phosphate, dimethyl methyl phosphate, phosphine oxide diol, triphenyl phosphate, tris-(2-chloroethyl) phosphate, phosphate esters such as tricreyl, trixylenyl, isodecyl diphenyl, ethylhexyl diphenyl, phosphate salts of various amines such as ammonium phosphate, trioctyl, tributyl or tris-butoxyethyl phosphate ester. Other suitable flame retardants may include tetraalkyl lead compounds such as tetraethyl lead, iron pentacarbonyl, manganese methyl cyclopentadienyl tricarbonyl, melamine and derivatives such as melamine salts, guanidine, dicyandiamide, ammonium sulphamate, alumina trihydrate, and magnesium hydroxide alumina trihydrate.

Aqueous compositions include any composition that includes water as a component, generally as a primary or majority component (e.g. as a solvent, carrier or medium). In these embodiments, the aqueous composition further comprises the copolymer of this disclosure.

As understood in the art, surfactants are compounds that lower the surface tension (or interfacial tension) between two liquids, between a gas and a liquid, or between a liquid and a solid. Surfactants may act as detergents, wetting agents, emulsifiers, foaming agents, and dispersants. Surfactants can serve as cleaning, wetting, dispersing, emulsifying, foaming and anti-foaming agents in many practical applications and products, including, but not limited to, detergents, fabric softeners, emulsions, soaps, paints, adhesives, inks, anti-fogs, ski waxes, snowboard wax, deinking of recycled papers, in flotation, washing and enzymatic processes, laxatives, etc. Agrochemical formulations such as some herbicides, insecticides, biocides (sanitizers), and spermicides may also include one or more surfactants. Personal care products such as cosmetics, shampoos, shower gel, hair conditioners (after shampoo), and toothpastes often include one or more surfactants.

In various embodiments, the surfactant composition comprises the copolymer of this disclosure. In certain embodiments, the surfactant composition further comprises one or more additives understood in the art, such as water and/or other vehicles, one or more conventional surfactants, etc. One of skill in the art appreciates that surfactant compositions may also be referred to as wetting compositions, surface tension modifiers, or dispersant compositions. In some applications, there may be slight nuances as to differences in form, function, and/or end application of such compositions.

In other embodiments, the copolymer itself is a surfactant. In these embodiments, the copolymer may be referred to as a dispersant, a wetting agent, or a surface tension modifier.

In various embodiments, the composition is selected from the group consisting of film-forming compositions, including foaming and substantially non-foaming compositions, aqueous and non-aqueous compositions, and combinations thereof. Certain films are described below. The composition may be curable, partially curable, or may not cure. In embodiments where the composition is at least partially curable to curable, the composition can change form, such as going from a liquid to a more viscous liquid, a gel, a semi-solid, or a solid.

In various embodiments, the composition is useful as an antiblocking (or anti-blocking) additive (or agent). In these embodiments, the composition may also provide scratch resistance and a low coefficient of friction (COF). In certain embodiments, the copolymer itself is the antiblocking additive.

Antiblocking agents are often used in or for films, e.g. in polyolefin films, to improve the slippage among individual molecules of the antiblocking agent and are important ingredients for the post-processing conversion (cutting, folding, welding etc.) of such films. Blocking is a common problem encountered by manufacturers of films and coatings. Blocking is the adhesion of two adjacent layers of film. It is a problem most associated with polyethylene and polypropylene films (either blown or cast) and to a lesser extent in extrusion coated or laminated products. Blocking of adjacent film layers occurs due to the presence of van der Waals forces between the amorphous regions of the polymer. These forces increase with reduced distance between the two layers, thereby increasing blocking when two layers are pressed together (e.g. binding onto a take up roll or stacking of finished, converted films). Another possible reason for blocking is the presence of low molecular weight species (such as oligomers) which tend to migrate to the surface of the film.

An effective method for combating these handling problems is to add an antiblocking additive. An antiblocking additive present in the resin microscopically protrudes from the film surface. This creates asperities ("little bumps") which help to minimize the film-to-film surface contact, increasing the distance between the two layers, thereby minimizing blocking.

The blocking between adjacent layers results in increased friction and the addition of an antiblocking agent generally contributes to a reduction in the film-to-film COF. COF is a measure of the relative difficulty with which one surface will slide over an adjoining surface. The greater the resistance to sliding, the higher the COF value (e.g. "low-slip" or "no-slip" films, sometimes referred to as "high COF" films).

In various embodiments, the composition is an agricultural composition. The copolymer can be used as an additive for the agricultural composition. Numerous types of compositions for facilitating agriculture are understood in the art, including those that promote plant grown, control or prevent weeds, control or prevent varmints and insects, etc. Whether using a plant growth regulator or a genetically altered plant, any number of agronomically suitable additives, adjuvants and/or phytocatalysts are applied to the plants to support or enhance plant growth, including: fertilizers containing elements such as nitrogen, phosphorus, potassium, elevated carbon dioxide, hydrogen peroxide, iron and manganese; secondary nutrients such as sources of sulfur, calcium, and magnesium; micronutrients, such as boron, cobalt, copper, molybdenum, zinc, nickel; water soluble carbohydrates such as sucrose, fructose and glucose; and various alkyl glucosides.

In various embodiments, the composition includes at least one pesticide. The term pesticide is understood to encompass herbicides, insecticides, acaricides, nematicides, ectoparasiticides, fungicides and plant growth regulators. The composition is not limited in this regard.

Examples of classes of compounds that have herbicidal activity include imidazolinones such as imazaquin, sulfonylureas such as chlorimuron-ethyl, triazolopyrimidine sulfonamides such as flumetsulam, aryloxyphenoxy propionates such as quizalofop ethyl, aryl ureas such as isoproturon and chlorotoluron, triazines such as atrazine and simazine, aryl carboxylic acids such as picloram, aryloxy alkanoic acids such as MCPA, chloroacetanilides such as metazachlor, dintroanilines such as oryzalin, pyrazoles such as pyrazolynate and diphenyl ethers such as bifenox. Examples of classes of compounds that have insecticidal activity include benzoyl ureas such as hexaflumuron, diacylhydrazines such as tebufenozide, carbamates such as carbofuran, pyrethroids such as cypermethrin, organophosphates such as phosmet, triazoles, and natural products such as spinosyns.

Examples of classes of compounds that have fungicidal activity include morpholines such as dimethomorph, phenylamides such as benalaxyl, azoles such as hexaconazole, strobilurins such as azoxystrobin, phthalonitriles such as chlorothalonil and phenoxyquinolines such as quinoxyfen.

Examples of insecticides/acaricides are benthiocarb, diflubenzuron, teflubenzuron, lufenuron, diafenthiuron or pyrethroide such as bifenthrin, bioallethrin, tau-fluvalinate, resmethrin, permethrin, cypermethrin, cyfluthrin, cyhalothrin, deltamethrin, tefluthrin or tetramethrin; furtheron pymetrozin, thiocyclam, fenoxycarb, methopren, abamectin and emamectin.

In various embodiments, the copolymer can be used for treatment of particles, for example, as intermediates to treat metal oxide particle surfaces. The particles can be of various sizes and particle size distributions, including nano- and micro-sized.

The metal oxide particles can be any suitable metal oxide particles. Suitable metal oxide particles include, for example, aluminum oxide, titanium oxide, silica, tin oxide, magnesium oxide, zinc oxide, strontium oxide particles, mixtures thereof, and co-oxides thereof.

The particles may be electrically and/or thermally conductive or non-conductive. In certain embodiments, the particles are classified as electrically conductive filler, which can be a metal or a conductive non-metal; or metal or non-metal particles having an outer surface of a metal, with the outer surface metal being a noble metal such as silver, gold, platinum, palladium, and alloys thereof, or a base metal such as nickel, aluminum, copper, or steel. The particles can also have an outer surface of a metal with a core of particles consisting of copper, solid glass, hollow glass, mica, nickel, ceramic fiber or polymeric such as polystyrene and polymethylmethacrylate.

In certain embodiments, the particles are classified as thermally conductive filler, which can be a metal particle, metal oxide particle, thermally conductive non-metal powder, or combinations thereof. The thermally conductive filler can be aluminum, copper, gold, nickel, silver, alumina, magnesium oxide, beryllium oxide, chromium oxide, titanium oxide, zinc oxide, barium titanate, diamond, graphite, carbon or silicon nano-sized particles, boron nitride, aluminum nitride, boron carbide, titanium carbide, silicon carbide, and tungsten carbide.

Examples of mineral fillers or pigments which can be treated include titanium dioxide, aluminium trihydroxide (also called ATH), magnesium dihydroxide, mica, kaolin, calcium carbonate, non-hydrated, partially hydrated, or hydrated fluorides, chlorides, bromides, iodides, chromates, carbonates, hydroxides, phosphates, hydrogen phosphates, nitrates, oxides, and sulphates of sodium, potassium, magnesium, calcium, and barium; zinc oxide, aluminium oxide, antimony pentoxide, antimony trioxide, beryllium oxide, chromium oxide, iron oxide, lithopone, boric acid or a borate salt such as zinc borate, barium metaborate or aluminium borate, mixed metal oxides such as aluminosilicate, vermiculite, silica including fumed silica, fused silica, precipitated silica, quartz, sand, and silica gel; rice hull ash, ceramic and glass beads, zeolites, metals such as aluminium flakes or powder, bronze powder, copper, gold, molybdenum, nickel, silver powder or flakes, stainless steel powder, tungsten, hydrous calcium silicate, barium titanate, silica-carbon black composite, functionalized carbon nanotubes, cement, fly ash, slate flour, ceramic or glass beads, bentonite, clay, talc, anthracite, apatite, attapulgite, boron nitride, cristobalite, diatomaceous earth, dolomite, ferrite, feldspar, graphite, calcined kaolin, molybdenum disulfide, perlite, pumice, pyrophyllite, sepiolite, zinc stannate, zinc sulphide or wollastonite.

Other fillers which may be treated include natural fibres such as wood flour, wood fibres, cotton fibres or agricultural fibres such as wheat straw, hemp, flax, kenaf, kapok, jute, ramie, sisal, henequen, corn fibre or coir, nut shells or rice hulls, lignin, starch, or cellulose and cellulose-containing products, or certain synthetic fibres such as aramid fibres, nylon fibres, cotton fibres or glass fibres, or plastic microspheres of polytetrafluoroethylene or polyethylene and the invention includes treatment of such fillers. The filler can be a solid organic pigment such as those incorporating azo, indigoid, triphenylmethane, anthraquinone, hydroquinone or xanthine dyes, or a solid organic flame retardant such as polychlorobiphenyl or decabromodiphenyl oxide or a phosphorus-containing flame retardant.

In various embodiments, the copolymer can be used to modify a siloxane or composition comprising at least one siloxane. The modification may be direct or indirect, such as in stances where the copolymer may react with the siloxane. Additional embodiments of the composition are described below.

The composition may include one or more fillers. The fillers may be one or more reinforcing fillers, non-reinforcing fillers, or mixtures thereof. Examples of finely divided, reinforcing fillers include high surface area fumed and precipitated silicas including rice hull ash and to a degree calcium carbonate. Examples of finely divided non-reinforcing fillers include crushed quartz, diatomaceous earths, barium sulphate, iron oxide, titanium dioxide and carbon black, talc, and wollastonite. Other fillers which might be used alone or in addition to the above include carbon nanotubes, e.g. multiwall carbon nanotubes aluminite, hollow glass spheres, calcium sulphate (anhydrite), gypsum, calcium sulphate, magnesium carbonate, clays such as kaolin, aluminum trihydroxide, magnesium hydroxide (brucite), graphite, copper carbonate, e.g. malachite, nickel carbonate, e.g. zarachite, barium carbonate, e.g. witherite and/or strontium carbonate e.g. strontianite. Further alternative fillers include aluminum oxide, silicates from the group consisting of olivine group; garnet group; aluminosilicates; ring silicates; chain silicates; and sheet silicates. In certain embodiments, the composition includes at least one filler comprising hollow particles, e.g. hollow spheres. Such fillers can be useful for contributing to porosity and/or overall void fraction of the foam. In certain embodiments, some fillers can be utilized to tune the thixotropic property of the composition.

The filler if present, may optionally be surface treated with a treating agent. Treating agents and treating methods are understood in the art. The surface treatment of the filler(s) is typically performed, for example with a fatty acid or a fatty acid ester such as a stearate, or with organosilanes, organosiloxanes, or organosilazanes such as hexaalkyi disilazane or short chain siloxane diols. Generally the surface treatment renders the filler(s) hydrophobic and therefore easier to handle and obtain a homogeneous mixture with the other components in the composition. Silanes such as $R^5{}_e Si(OR^6)_{4-e}$ where $R^5$ is a substituted or unsubstituted monovalent hydrocarbon group of 6 to 20 carbon atoms, for example, alkyl groups such as hexyl, octyl, dodecyl, tetradecyl, hexadecyl, and octadecyl, and aralkyl groups such as benzyl and phenylethyl, $R^6$ is an alkyl group of 1 to 6 carbon atoms, and subscript "e" is equal to 1, 2 or 3, may also be utilized as the treating agent for fillers. In certain embodiments, the copolymer can used as a treating agent as described above, optionally in combination with one or more conventional treating agents.

In various embodiments, the composition further comprises a reaction inhibitor. For example, an alkyne alcohol such as 2-methyl-3-butyn-2-ol, 3,5-dimethyl-1-hexyn-3-ol, or 2-phenyl-3-butyn-2-ol; an ene-yne compound such as 3-methyl-3-penten-1-yne or 3,5-dimethyl-3-hexen-1-yne; or 1,3,5,7-tetramethyl-1,3,5,7-tetravinylcyclotetrasiloxane, 1,3,5,7-tetramethyl-1,3,5,7-tetrahexenylcyclotetrasiloxane, or a benzotriazole may be incorporated as an optional component in the composition.

In various embodiments, the composition further comprises a thixotropic agent. Suitable thixotropic agents include rheological agents, specific examples of such agents may be found in U.S. Pub. Nos. 2018/0066115 A1 and 2018/0208797 A1.

In various embodiments, the composition further comprises an adhesion-imparting agent. The adhesion-imparting agent can improve adhesion of the foam to a base material being contacted during curing, e.g. the second surface 36. In certain embodiments, the adhesion-imparting agent is selected from organosilicon compounds having at least one alkoxy group bonded to a silicon atom in a molecule. This alkoxy group is exemplified by a methoxy group, an ethoxy group, a propoxy group, a butoxy group, and a methoxyethoxy group. Moreover, non-alkoxy groups bonded to a silicon atom of this organosilicon compound are exemplified by substituted or non-substituted monovalent hydrocarbon groups such as alkyl groups, alkenyl groups, aryl groups, aralkyl groups, halogenated alkyl groups and the like; epoxy group-containing monovalent organic groups such as a 3-glycidoxypropyl group, a 4-glycidoxybutyl group, or similar glycidoxyalkyl groups; a 2-(3,4-epoxycyclohexyl) ethyl group, a 3-(3,4-epoxycyclohexyl)propyl group, or similar epoxycyclohexylalkyl groups; and a 4-oxiranylbutyl group, an 8-oxiranyloctyl group, or similar oxiranylalkyl groups; acrylic group-containing monovalent organic groups such as a 3-methacryloxypropyl group and the like; and a hydrogen atom.

This organosilicon compound generally has a silicon-bonded alkenyl group or silicon-bonded hydrogen atom. Moreover, due to the ability to impart good adhesion with respect to various types of base materials, this organosilicon compound generally has at least one epoxy group-containing monovalent organic group in a molecule. This type of organosilicon compound is exemplified by organosilane compounds, organosiloxane oligomers and alkyl silicates. Molecular structure of the organosiloxane oligomer or alkyl silicate is exemplified by a linear chain structure, partially branched linear chain structure, branched chain structure, ring-shaped structure, and net-shaped structure. A linear chain structure, branched chain structure, and net-shaped structure are typical. This type of organosilicon compound is exemplified by silane compounds such as 3-glycidoxypropyltrimethoxysilane, 2-(3,4-epoxycyclohexyl)-ethyltrimethoxysilane, 3-methacryloxy propyltrimethoxysilane, and the like; siloxane compounds having at least one silicon-bonded alkenyl group or silicon-bonded hydrogen atom, and at least one silicon-bonded alkoxy group in a molecule; mixtures of a silane compound or siloxane compound having at least one silicon-bonded alkoxy group and a siloxane compound having at least one silicon-bonded hydroxy group and at least one silicon-bonded alkenyl group in the molecule; and methyl polysilicate, ethyl polysilicate, and epoxy group-containing ethyl polysilicate.

In various embodiments, the composition includes at least one blowing agent. If utilized, the blowing agent can be selected from the group of chemical blowing agents, physical blowing agents, and combinations thereof. The amount of blowing agent utilized can vary depending on the desired outcome. For example, the amount of blowing agent can be varied to tailor final foam density and foam rise profile.

The composition can include carrier vehicles (or diluents) include silicones, both linear and cyclic, organic oils, organic solvents and mixtures of these. Specific examples of solvents may be found in U.S. Pat. No. 6,200,581. The carrier vehicle may also be a low viscosity organopolysiloxane or a volatile methyl siloxane or a volatile ethyl siloxane or a volatile methyl ethyl siloxane having a viscosity at 25° C. in the range of 1 to 1,000 mm$^2$/sec, such as hexamethylcyclotrisiloxane, octamethylcyclotetrasiloxane, ecamethylcyclopentasiloxane, dodecamethylcyclohexasiloxane, octamethyltrisiloxane, decamethyltetrasiloxane, dodecamethylpentasiloxane, tetradecamethylhexasiloxane, exadeamethylheptasiloxane, heptamethyl-3-{(trimethylsilyl)oxy)}trisiloxane, hexamethyl-3,3,bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes, caprylyl methicone, and any mixtures thereof.

In some embodiments, the composition comprises one or more additional components, such as a rheology modifier, a polar organic solvent, a thickener, an inorganic salt (e.g. calcium chloride), a personal care active/ingredient, a fragrance, or combinations thereof. Typically, the one or more additional components are selected based on a desired use of the composition. For example, in some embodiments the composition is formulated for use as a personal care composition and further comprises a personal care ingredient. The specific personal care ingredient, or a mixture of specific personal care ingredients, may be selected based on the type of personal care composition the composition is being formulated as. In these embodiments, the personal care ingredient may be a liquid, a solid, an encapsulated liquid, etc. Various examples of the personal care ingredient are described below. Any of these personal care ingredients, or a combination of two or more different personal care ingredients, may be utilized as the personal care ingredient. For clarity and consistency, "the personal care ingredient" encompasses embodiments where the composition includes but one or two or more personal care ingredients.

In specific embodiments, the personal care ingredient is an antiperspirant and/or deodorant (AP/DEO) agent. In these embodiments, the composition may be referred to as an antiperspirant and/or deodorant (AP/DEO) composition. Examples of antiperspirant agents and deodorant agents include aluminum chloride, aluminum zirconium tetrachlorohydrex GLY, aluminum zirconium tetrachlorohydrex PEG, aluminum chlorohydrex, aluminum zirconium tetrachlorohydrex PG, aluminum chlorohydrex PEG, aluminum zirconium trichlorohydrate, aluminum chlorohydrex PG, aluminum zirconium trichlorohydrex GLY, hexachlorophene, benzalkonium chloride, aluminum sesquichlorohydrate, sodium bicarbonate, aluminum sesquichlorohydrex PEG, chlorophyllin-copper complex, triclosan, aluminum zirconium octachlorohydrate, zinc ricinoleate, and mixtures thereof.

In certain embodiments, the personal care ingredient comprises a skin care ingredient. If utilized to prepare the composition, the skin care ingredient is typically selected from water phase stabilizing agents, cosmetic biocides, conditioning agents (which may be silicone, cationic, hydrophobic, etc.), emollients, moisturizers, colorants, dyes, ultraviolet (UV) absorbers, sunscreen agents, antioxidants, fragrances, antimicrobial agents, antibacterial agents, antifungal agents, antiaging actives, anti-acne agents, skin-lightening agents, pigments, preservatives, pH controlling agents, electrolytes, chelating agents, plant extracts, botanical extracts, sebum absorbents, sebum control agents, vitamins, waxes, surfactants, detergents, emulsifiers, thickeners, propellant gases, skin protectants, film forming polymers, light scattering agents, and combinations thereof. In some of these embodiments, the composition may be referred to as a skin care composition, a cosmetic composition, a sunscreen, a shower gel, a soap, a hydrogel, a cream, a lotion, a balm, foundation, lipstick, eyeliner, a cuticle coat, a blush, etc., based on the particular personal care ingredients utilized. Various species of such skin care ingredients are set forth below, with similar and alternative species known by one of ordinary skill in the art.

Examples of emollients include volatile or non-volatile silicone oils; silicone resins such as polypropylsilsesquioxane and phenyl trimethicone; silicone elastomers such as dimethicone crosspolymer; alkylmethylsiloxanes such as $C_{30-45}$ alkyl methicone; volatile or non-volatile hydrocarbon compounds, such as squalene, paraffin oils, petrolatum oils and naphthalene oils; hydrogenated or partially hydrogenated polyisobutene; isoeicosane; squalane; isoparaffin; isododecane; isodecane or isohexa-decane; branched $C_8$-$C_{16}$ esters; isohexyl neopentanoate; ester oils such as isononyl isononanoate, cetostearyl octanoate, isopropyl myristate, palmitate derivatives (e.g. dextrin palmitate), stearates derivatives, diisostearyl malate, isostearyl isostearate and the heptanoates, octanoates, decanoates or ricinoleates of alcohols or of polyalcohols, or mixtures thereof; hydrocarbon oils of plant origin, such as wheatgerm, sunflower, grapeseed, castor, shea, avocado, olive, soybean, sweet almond, palm, rapeseed, cotton seed, hazelnut, macadamia, jojoba, blackcurrant, evening primrose; or triglycerides of caprylic/capric acids; higher fatty acids, such as oleic acid, linoleic acid or linolenic acid, and mixtures thereof.

Examples of waxes include hydrocarbon waxes such as beeswax, lanolin wax, rice wax, carnauba wax, candelilla wax, microcrystalline waxes, paraffins, ozokerite, polyethylene waxes, synthetic wax, ceresin, lanolin, lanolin derivatives, cocoa butter, shellac wax, bran wax, capok wax, sugar cane wax, montan wax, whale wax, bayberry wax, silicone waxes (e.g. polymethylsiloxane alkyls, alkoxys and/or esters, $C_{30-45}$ alkyldimethylsilyl polypropylsilsesquioxane), stearyl dimethicone, alkylmethylsiloxanes including long-chain alkyl groups in alkylmethylsiloxy units, and mixtures thereof.

Examples of moisturizers include lower molecular weight aliphatic diols such as propylene glycol and butylene glycol; polyols such as glycerine and sorbitol; and polyoxyethylene polymers such as polyethylene glycol 200; hyaluronic acid and its derivatives, and mixtures thereof.

Examples of thickeners include acrylamide copolymers, acrylate copolymers and salts thereof (such as sodium polyacrylate), xanthan gum and derivatives, cellulose gum and cellulose derivatives (such as methylcellulose, methylhydroxypropylcellulose, hydroxyethylcellulose, hydroxypropylcellulose, polypropylhydroxyethylcellulose), starch and starch derivatives (such as hydroxyethylamylose and starch amylase), polyoxyethylene, carbomer, alginates (such as sodium alginate), arabic gum, cassia gum, carob gum, scleroglucan gum, gellan gum, rhamsan gum, karaya gum, carrageenan gum, guar gum and guar gum derivatives, cocamide derivatives (including cocamidopropyl betaine and cocamide MIPA), alkyl alcohols (such as cetearyl alcohol, stearyl alcohol, and other fatty alcohols), gelatin, PEG-derivatives, saccharides (such as fructose, glucose) and saccharides derivatives (such as PEG-120 methyl glucose diolate), and mixtures thereof.

Examples of water phase stabilizing agents include electrolytes (e.g. alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate), polyols (glycerine, propylene glycol, butylene glycol, and sorbitol), alcohols such as ethyl alcohol, and hydrocolloids, and mixtures thereof.

Examples of pH controlling agents include any water soluble acid such as a carboxylic acid or a mineral acid such as hydrochloric acid, sulphuric acid, and phosphoric acid, monocarboxylic acid such as acetic acid and lactic acid, and polycarboxylic acids such as succinic acid, adipic acid, citric acid, and mixtures thereof.

Example of preservatives and cosmetic biocides include paraben derivatives (e.g. methylparaben, propylparaben), hydantoin derivatives, chlorhexidine and its derivatives, imidazolidinyl urea, diazolidinyl urea, phenoxyethanol, silver derivatives, salicylate derivatives, triclosan, ciclopirox olamine, hexamidine, oxyquinoline and its derivatives, PVP-iodine, zinc salts and derivatives such as zinc pyrithione, methylchloroisothiazolinone, methylisothiazolinone, and mixtures thereof.

Examples of sebum absorbants or sebum control agents include silica silylate, silica dimethyl silylate, dimethicone/vinyl dimethicone crosspolymer, polymethyl methacrylate, cross-linked methylmethacrylate, aluminum starch octenylsuccinate, and mixtures thereof.

Examples of pigments and colorants include surface treated or untreated iron oxides, surface treated or untreated titanium dioxide, surface treated or untreated mica, silver oxide, silicates, chromium oxides, carotenoids, carbon black, ultramarines, chlorophyllin derivatives and yellow ocher. Examples of organic pigments include aromatic types including azo, indigoid, triphenylmethane, anthraquinone, and xanthine dyes which are designated as D&C and FD&C blues, browns, greens, oranges, reds, yellows, etc, and mixtures thereof. Surface treatments include those treatments based on lecithin, silicone, silanes, fluoro compounds, and mixtures thereof.

Examples of silicone conditioning agents include silicone oils such as dimethicone; silicone gums such as dimethiconol; silicone resins such as trimethylsiloxy silicate, polypropyl silsesquioxane; silicone elastomers; alkylmethylsiloxanes; organomodified silicone oils, such as amodimethicone, aminopropyl phenyl trimethicone, phenyl trimethicone, trimethyl pentaphenyl trisiloxane, silicone quaternium-16/glycidoxy dimethicone crosspolymer, silicone quaternium-16; saccharide functional siloxanes; carbinol functional siloxanes; silicone polyethers; siloxane copolymers (divinyldimethicone/dimethicone copolymer); acrylate or acrylic functional siloxanes; and mixtures or emulsions thereof.

Examples of cationic conditioning agents include guar derivatives such as hydroxypropyltrimethylammonium derivative of guar gum; cationic cellulose derivatives, cationic starch derivatives; quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polymeric quaternary ammonium salts of hydroxyethyl cellulose reacted with a fatty alkyl dimethyl ammonium substituted epoxide; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats, e.g. Polyquaternium-7, Polyquaternium-8, Polyquaternium-10, Polyquaternium-11, and Polyquaternium-23. Other categories of conditioners include cationic surfactants such as cetyl trimethylammonium chloride, cetyl trimethylammonium bromide, stearyltrimethylammonium chloride, and mixtures thereof. In some instances, the cationic conditioning agent is also hydrophobically modified, such as hydrophobically modified quaternized hydroxyethylcellulose polymers; cationic hydrophobically modified galactomannan ether; and mixtures thereof.

Examples of hydrophobic conditioning agents include guar derivatives; galactomannan gum derivatives; cellulose derivatives; and mixtures thereof.

UV absorbers and sunscreen agents include those which absorb ultraviolet light between 290-320 nanometers (the UV-B region) and those which absorb ultraviolet light in the range of 320-400 nanometers (the UV-A region).

Some examples of sunscreen agents are aminobenzoic acid, cinoxate, diethanolamine methoxycinnamate, digalloyl trioleate, dioxybenzone, ethyl 4-[bis(Hydroxypropyl)]aminobenzoate, glyceryl aminobenzoate, homosalate, lawsone with dihydroxyacetone, menthyl anthranilate, octocrylene, ethylhexyl methoxycinnamate (or octyl methoxycinnamate), octyl salicylate (or ethylhexyl salicylate), oxybenzone, padimate O, phenylbenzimidazole sulfonic acid, red petrolatum, sulisobenzone, titanium dioxide, trolamine salicylate, and mixtures thereof.

Some examples of UV absorbers are acetaminosalol, allatoin PABA, benzalphthalide, benzophenone, benzophenone 1-12, 3-benzylidene camphor, benzylidenecamphor hydrolyzed collagen sulfonamide, benzylidene camphor sulfonic Acid, benzyl salicylate, bornelone, bumetriozole, butyl methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium distyrylbiphenyl triaminotriazine stilbenedisulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, octyl methoxycinnamate, menthyl anthranilate, menthyl salicylate, 4-methylbenzylidene, camphor, octocrylene, octrizole, octyl dimethyl PABA, ethyl hexyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, triPABA panthenol, urocanic acid, VA/crotonates/methacryloxybenzophenone-1 copolymer, and mixtures thereof.

Examples of skin protectants include allantoin, aluminium acetate, aluminium hydroxide, aluminium sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, zinc oxide, and mixtures thereof.

Examples of dyes include 1-acetoxy-2-methylnaphthalene; acid dyes; 5-amino-4-chloro-o-cresol; 5-amino-2,6-dimethoxy-3-hydroxypyridine; 3-amino-2,6-dimethylphenol; 2-amino-5-ethylphenol HCl; 5-amino-4-fluoro-2-methylphenol sulfate; 2-amino-4-hydroxyethylaminoanisole; 2-amino-4-hydroxyethylaminoanisole sulfate; 2-amino-5-nitrophenol; 4-amino-2-nitrophenol; 4-amino-3-nitrophenol; 2-amino-4-nitrophenol sulfate; m-aminophenol HCl; p-aminophenol HCl; m-aminophenol; o-aminophenol; 4,6-bis(2-hydroxyethoxy)-m-phenylenediamine HCl; 2,6-bis(2-hydroxyethoxy)-3,5-pyridinediamine HCl; 2-chloro-6-ethylamino-4-nitrophenol; 2-chloro-5-nitro-N-hydroxyethyl p-phenylenediamine; 2-chloro-p-phenylenediamine; 3,4-diaminobenzoic acid; 4,5-diamino-1-((4-chlorophenyl)methyl)-1H-pyrazole-sulfate; 2,3-diaminodihydropyrazolo pyrazolone dimethosulfonate; 2,6-diaminopyridine; 2,6-diamino-3-((pyridin-3-yl)azo)pyridine; dihydroxyindole; dihydroxyindoline; N,N-dimethyl-p-phenylenediamine; 2,6-dimethyl-p-phenylenediamine; N,N-dimethyl-p-phenylenediamine sulfate; direct dyes; 4-ethoxy-m-phenylenediamine sulfate; 3-ethylamino-p-cresol sulfate; N-ethyl-3-nitro PABA; gluconamidopropyl aminopropyl dimethicone; *Haematoxylon brasiletto* wood extract; HC dyes; *Lawsonia inermis* (Henna) extract; hydroxyethyl-3,4-methylenedioxyaniline HCl; hydroxyethyl-2-nitro-p-toluidine; hydroxyethyl-p-phenylenediamine sulfate; 2-hydroxyethyl picramic acid; hydroxypyridinone; hydroxysuccinimidyl $C_{21}$-$C_{22}$ isoalkyl acidate; isatin; *Isatis tinctoria* leaf powder; 2-methoxymethyl-p-phenylenediamine sulfate; 2-methoxy-p-phenylenediamine sulfate; 6-methoxy-2,3-pyridinediamine HCl; 4-methylbenzyl 4,5-diamino pyrazole sulfate; 2,2'-methylenebis 4-aminophenol; 2,2'-methylenebis-4-aminophenol HCl; 3,4-methylenedioxyaniline; 2-methylresorcinol; methylrosanilinium chloride; 1,5-naphthalenediol; 1,7-naphthalenediol; 3-nitro-p-Cresol; 2-nitro-5-glyceryl methylaniline; 4-nitroguaiacol; 3-nitro-p-hydroxyethylaminophenol; 2-nitro-N-hydroxyethyl-p-anisidine; nitrophenol; 4-nitrophenyl aminoethylurea; 4-nitro-o-phenylenediamine dihydrochloride; 2-nitro-p-phenylenediamine dihydrochloride; 4-nitro-o-phenylenediamine HCl; 4-nitro-m-phenylenediamine; 4-nitro-o-phenylenediamine; 2-nitro-p-phenylenediamine; 4-nitro-m-phenylenediamine sulfate; 4-nitro-o-phenylenediamine sulfate; 2-nitro-p-phenylenediamine sulfate; 6-nitro-2,5-pyridinediamine; 6-nitro-o-toluidine; PEG-3 2,2'-di-p-phenylenediamine; p-phenylenediamine HCl; p-phenylenediamine sulfate; phenyl methyl pyrazolone; N-phenyl-p-phenylenediamine HCl; pigment blue 15:1; pigment violet 23; pigment yellow 13; pyrocatechol; pyrogallol; resorcinol; sodium picramate; sodium sulfanilate; solvent yellow 85; solvent yellow 172; tetraaminopyrimidine sulfate; tetrabromophenol blue; 2,5,6-triamino-4-pyrimidinol sulfate; 1,2,4-trihydroxybenzene.

Examples of fragrances include perfume ketones and perfume aldehydes. Illustrative of the perfume ketones are buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-Ionone, Beta-Ionone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethyl-Cyclohexanone, Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbornane, 6,7-Dihydro-1,1,2,3,3-

Pentamethyl-4(5H)-Indanone, 4-Damascol, Dulcinyl or Cassione, Gelsone, Hexylon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran. The fragrance may be derived or extracted from flowers, seeds, leaves, and/or roots of plants, seaweed, etc. The fragrance may be extracted from an animal, e.g. from a secretion gland, and may be a musk or sperm oil. The fragrance may also be artificially synthesized, e.g. menthol, acetate, vanilla, etc.

In specific embodiments, the perfume ketones are selected for odor character from Alpha Damascone, Delta Damascone, Iso Damascone, Carvone, Gamma-Methyl-Ionone, Iso-E-Super, 2,4,4,7-Tetramethyl-oct-6-en-3-one, Benzyl Acetone, Beta Damascone, Damascenone, methyl dihydrojasmonate, methyl cedrylone, and mixtures thereof.

In specific embodiments, the perfume aldehyde is selected for odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, dihydrocinnamic aldehyde, 1-methyl-4-(4-methyl-3-pentenyl)-3-cyclohexene-1-carboxaldehyde, 5 or 6 methoxy hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyloctanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butenal, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl)benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

Examples of antioxidants are acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, *Camellia sinensis* oil, chitosan ascorbate, chitosan glycolate, chitosan salicylate, chlorogenic acids, cysteine, cysteine HCl, decyl mercaptomethylimidazole, erythorbic acid, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (*Melaleuca aftemifolia*) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, zinc dibutyldithiocarbamate, and mixtures thereof.

Examples of propellant gases include carbon dioxide, nitrogen, nitrous oxide, volatile hydrocarbons such as butane, isobutane, or propane, and chlorinated or fluorinated hydrocarbons such as dichlorodifluoromethane and dichlorotetrafluoroethane or dimethylether; and mixtures thereof.

In a specific embodiment, the composition is a sunscreen. In these embodiments, personal care ingredient comprises the sunscreen agent. The sunscreen agent may be, for example, a sunscreen additive, an SPF booster, a photostabilizer, a film-forming polymer, etc. The sunscreen may be also or alternatively be utilized in sunless tanning applications. Specific examples of sunscreen agents are set forth above.

In other embodiments, the personal care ingredient comprises a hair care ingredient. In these embodiments, the composition may be referred to as a hair care composition. If utilized to prepare the composition, the hair care ingredient is typically selected from conditioning agents (which may be silicone, cationic, hydrophobic, etc.), colorants, dyes, ultraviolet (UV) absorbers, preservatives, plant extracts, fatty alcohols, vitamins, fragrance, anti-dandruff agents, color care additives, pearlising agents, pH controlling agents, electrolytes, chelating agents, styling agents, ceramides, amino-acid derivatives, suspending agents, surfactants, detergents, emulsifiers, thickeners, oxidizing agents, reducing agents, film-forming polymers, and combinations thereof. With some of these hair care embodiments, the composition may be referred to as a shampoo, a rinse-off conditioner, a leave-in conditioner, a gel, a pomade, a serum, a spray, a coloring product, or mascara. Examples of many of these hair care ingredients are set forth above as suitable personal care ingredients.

Examples of oxidizing agents are ammonium persulfate, calcium peroxide, hydrogen peroxide, magnesium peroxide, melamine peroxide, potassium bromate, potassium caroate, potassium chlorate, potassium persulfate, sodium bromate, sodium carbonate peroxide, sodium chlorate, sodium iodate, sodium perborate, sodium persulfate, strontium dioxide, strontium peroxide, urea peroxide, zinc peroxide, and mixtures thereof.

Examples of reducing agents are ammonium bisufite, ammonium sulfite, ammonium thioglycolate, ammonium thiolactate, cystemaine HCl, cystein, cysteine HCl, ethanolamine thioglycolate, glutathione, glyceryl thioglycolate, glyceryl thioproprionate, hydroquinone, p-hydroxyanisole, isooctyl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, superoxide dismutase, thioglycerin, thioglycolic acid, thiolactic acid, thiosalicylic acid, zinc formaldehyde sulfoxylate, and mixtures thereof.

Examples of antidandruff agents include pyridinethione salts, selenium compounds such as selenium disulfide, and soluble antidandruff agents, and mixtures thereof.

In other embodiments, the personal care ingredient comprises a nail care ingredient. In these embodiments, the composition may be referred to as a nail care composition. If utilized to prepare the composition, the nail care ingredient may be any ingredient utilized in nail care compositions, e.g. nail polishes, nail gels, nail tips, acrylic finishes, etc. Examples of such nail care ingredients include pigments, resins, solvents, volatile halogenated compounds (e.g. methoxynonafluorobutane and/or ethoxynonafluorobutane), etc.

More specifically, examples of nail care ingredients include butyl acetate; ethyl acetate; nitrocellulose; acetyl tributyl citrate; isopropyl alcohol; adipic acid/neopentyl glycol/trimelitic anhydride copolymer; stearalkonium bentonite; acrylates copolymer; calcium pantothenate; *Cetraria islandica* extract; *Chondrus crispus*; styrene/acrylates copolymer; trimethylpentanediyl dibenzoate-1; polyvinyl butyral; N-butyl alcohol; propylene glycol; butylene glycol; mica; silica; tin oxide; calcium borosilicate; synthetic fluorphlogopite; polyethylene terephtalate; sorbitan laurate derivatives; talc; jojoba extract; diamond powder; isobutylphenoxy epoxy resin; silk powder; and mixtures thereof.

In other embodiments, the personal care ingredient comprises a tooth care ingredient. In these embodiments, the composition may be referred to as a tooth care composition. One specific example of such a tooth care composition is toothpaste. Another example of a tooth care composition is a tooth whitening composition. The tooth care ingredient may be any tooth care ingredient suitable for the tooth care composition, such as an abrasive compound (e.g. aluminum hydroxide, calcium carbonate, silica, zeolite), a fluoride compound, a surfactant, a flavorant, a remineralizer, an antibacterial agent, etc.

In certain embodiments, the personal care ingredient comprises a film-forming polymer, which may be utilized as the personal care ingredient whether the composition is utilized for skin care, hair care, etc. "Film-forming polymer," as used herein, means a polymer or oligomer which is capable of, by itself or optionally in the presence of a film-forming agent, forming a film on a substrate. The film-forming polymer may form the film upon an application of a curing condition, e.g. the application of heat, exposure to atmospheric conditions, etc. Alternatively, the film-forming polymer may form the film upon evaporation of any carrier vehicle in which the film-forming polymer may optionally be disposed. The film-forming polymer may undergo a reaction, e.g. the film-forming polymer may become cross-linked or otherwise include additional bonds, when forming the film. However, the film-forming polymer may form the film in the absence of such a reaction. The film-forming polymer may be a gelling agent. The film-forming polymer is particularly advantageous when the composition is the sunscreen, although the personal care ingredient may comprise the film-forming polymer in other compositions as well.

The substrate on which the film is formed may be any substrate, although the substrate is generally a portion of a mammal, particularly a human, as described in greater detail below with reference to the treatment method. Specific examples of suitable substrates include skin, hair, and nails.

Generally, the film is continuous, although the film may have a varying thickness. By continuous, it is meant that the film does not define any apertures. The film may be referred to as being macroscopically continuous. The film may be supported by the substrate, or may be bonded, e.g. physically and/or chemically, to the substrate. In certain embodiments, the film is optionally removable from the substrate, e.g. the film may be peelable from the substrate. The film may remain intact as a free-standing film upon being separated from the substrate or may be separated through application of shear, which may damage and/or destroy continuity of the film.

Specific examples of film-forming polymers that are suitable include acrylic polymers, silicone resins (e.g. polypropylsilsesquioxane), polyurethanes, polyurethane-acrylics, polyesters, polyester-polyurethanes, polyether-polyurethanes, polyesteramides, alkyds, polyamides, polyureas, polyurea-polyurethanes, cellulose-based polymers (e.g. nitrocellulose), silicones, acrylic-silicones, polyacrylamides, fluoropolymers, polyisoprenes, and any copolymers or terpolymers thereof or including one of these. The term "silicones," as used herein with reference to suitable film-forming polymers, includes linear, branched, and resinous silicones, although resinous silicones are generally referred to as silicone resins rather than polymers. The silicone may be modified, e.g. the silicone may be a silicone-grafted acrylic polymer.

As introduced above, the film-forming polymer may be disposed in a carrier vehicle, which may partially or fully solubilize the film-forming polymer. Depending on a selection of the film-forming polymer, the carrier vehicle may be, for example, an oil, e.g. an organic oil and/or a silicone oil, a solvent, water, etc. The film-forming polymer may be in the form of polymer particles, which are optionally surface-stabilized with at least one stabilizer, and the polymer particles may be present as a dispersion or emulsion.

The film-forming polymer may be a block polymer, which may be styrene-free. Typically, the block polymer comprises at least one first block and at least one second block, which may be linked together via an intermediate block comprising at least one constituent monomer of the first block and at least one constituent monomer of the second block. Generally, the glass transition temperatures of the first and second blocks are different from one another.

Monomers that may be utilized to prepare the block polymer include, for example, methyl methacrylate, isobutyl (meth)acrylate and isobornyl (meth)acrylate, methyl acrylate, isobutyl acrylate, n-butyl methacrylate, cyclodecyl acrylate, neopentyl acrylate, isodecylacrylamide 2-ethylhexyl acrylate and mixtures thereof.

In specific embodiments, the film-forming polymer be obtained or generated via free-radical polymerization. For example, the film-forming polymer may be generated via free-radical polymerization of at least one acrylic monomer and at least one silicone- or hydrocarbon-based macromonomer including a polymerizable end group.

Specific examples of hydrocarbon-based macromonomers include homopolymers and copolymers of linear or branched $C_8$-$C_{22}$ alkyl acrylate or methacrylate. The polymerizable end group may be a vinyl group or a (meth)acrylate group, e.g. poly(2-ethylhexyl acrylate) macromonomers; poly(dodecyl acrylate) or poly(dodecyl methacrylate) macromonomers; poly(stearyl acrylate) or poly(stearyl methacrylate) macromonomers, etc. Such macromonomers generally include one (meth)acrylate group as the polymerizable end group.

Additional examples of hydrocarbon-based macromonomers include polyolefins containing an ethylenically unsaturated end group (as the polymerizable end group), e.g. a (meth)acrylate end group. Specific examples of such polyolefins include polyethylene macromonomers, polypropylene macromonomers, polyethylene/polypropylene copolymer macromonomers, polyethylene/polybutylene copolymer macromonomers, polyisobutylene macromonomers; polybutadiene macromonomers; polyisoprene macromonomers; polybutadiene macromonomers; and poly (ethylene/butylene)-polyisoprene macromonomers.

Examples of silicone-based macromonomers include organopolysiloxanes containing the polymerizable end group, e.g. a (meth)acrylate end group. The organopolysiloxane may be linear, branched, partially branched, or resinous. In various embodiments, the organopolysiloxane is linear. In these embodiments, the organopolysiloxane may be polydimethylsiloxane, although hydrocarbon groups other than methyl groups may be present therein along with or in lieu of methyl groups. Typically, the polymerizable end group is terminal, although the polymerizable end group may optionally be pendant. One specific example of a silicone-based macromonomer is a monomethacryloxypropyl polydimethylsiloxane.

In certain embodiments, the film-forming polymer is an organic film-forming polymer that is soluble in oil as the carrier vehicle. In these embodiments, the film-forming polymer may be referred to as a liposoluble polymer. The liposoluble polymer may be of any type and specific examples thereof include those comprising or formed from olefins, cycloolefins, butadiene, isoprene, styrene, vinyl ethers, vinyl esters, vinyl amides, (meth)acrylic acid esters or amides, etc.

In one embodiment, the liposoluble polymer is formed from monomers selected from the group consisting of isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth) acrylate, stearyl (meth)acrylate, and combinations thereof.

Alternatively still, the liposoluble polymer may be an acrylic-silicone grafted polymer, which typically includes a silicone backbone and acrylic grafts or alternatively includes an acrylic backbone and silicone grafts.

The film-forming polymer may be halogenated, e.g. the film-forming polymer may include fluorine atoms.

Alternatively as introduced above, the film-forming polymer may be a cellulose-based polymer, such as nitrocellulose, cellulose acetate, cellulose acetobutyrate, cellulose acetopropionate or ethylcellulose. Alternatively still, the film-forming polymer may comprise a polyurethane, an acrylic polymer, a vinyl polymer, a polyvinyl butyral, an alkyd resin, or resins derived from aldehyde condensation products, such as arylsulfonamide-formaldehyde resins.

Further, as introduced above, the film-forming polymer may comprise the silicone, which may be linear, branched, or resinous. Resinous silicones generally include at least one T and/or Q unit, as understood in the art. Examples of resinous silicones include silsesquioxanes. The silicone may include any combination of M, D, T, and Q units so long as the silicone constitutes the film-forming polymer.

When the film-forming polymer comprises the silicone, the film-forming polymer may comprise an amphiphilic silicone. Amphiphilic silicones typically contain a silicone portion which is compatible with a silicone medium, and a hydrophilic portion. The hydrophilic portion may be, for example, the residue of a compound selected from alcohols and polyols, having 1 to 12 hydroxyl groups, and polyoxyalkylenes (e.g. those containing oxypropylene units and/or oxyethylene units).

The amphiphilic silicone may be an oil with or without gelling activity. Oils of this kind may comprise, for example, dimethicone copolyols, bis-hydroxyethoxypropyl dimethicone, etc.

In one embodiment, the film-forming polymer comprises a silicone organic elastomer gel. Silicone organic elastomer gels comprise linear organopolysiloxane chains crosslinked via polyoxyalkylenes. The silicone organic elastomer gel may further include hydrophilic polyether functionality pending from the linear organopolysiloxane chains. Specific examples of suitable silicone organic elastomer gels are disclosed in International (PCT) Appln. No. PCT/US2010/020110.

In various embodiments, the personal care ingredient may comprise or be referred to as a personal care active, a health care active, or combination thereof (collectively "active" or "actives"). As used herein, a "personal care active" means any compound or mixtures of compounds that are known in the art as additives in personal care formulations, typically for providing a cosmetic and/or aesthetic benefit. A "healthcare active" means any compound or mixtures of compounds that are known in the art to provide a pharmaceutical or medical benefit. Thus, "healthcare active" includes materials considered as an active ingredient or active drug ingredient as generally used and defined by the United States Department of Health & Human Services Food and Drug Administration, contained in Title 21, Chapter I, of the Code of Federal Regulations, Parts 200-299 and Parts 300-499. Specific personal care actives and health care actives are described below. These personal care actives and health care actives may constitute the personal care ingredient whether the personal care ingredient is utilized to form, for example, the AP/DEO composition, the skin care composition, the hair care composition, the nail care composition, and/or the tooth care composition. For example, in various embodiments, the same personal care ingredient may be utilized to form either the hair care composition or the skin care composition. As understood in the art, at least some of the personal care actives described below are species of certain personal care ingredients introduced above with respect to the skin care composition, the hair care composition, the nail care composition, and the tooth care composition, respectively. For example, numerous species of plant or vegetable extracts are described below, which are exemplary examples of plant extracts set forth above as suitable personal care ingredients. The active ingredients or actives described below may constitute the personal care ingredient of the composition or may be utilized in combination therewith.

Useful active ingredients for use in the composition include vitamins and vitamin derivatives, including "provitamins". Vitamins useful herein include, but are not limited to, Vitamin A1, retinol, $C_2$-$C_{18}$ esters of retinol, vitamin E, tocopherol, esters of vitamin E, and mixtures thereof. Retinol includes trans-retinol, 1,3-cis-retinol, 11-cis-retinol, 9-cis-retinol, and 3,4-didehydro-retinol, Vitamin C and its derivatives, Vitamin B1, Vitamin B2, Pro Vitamin B5, panthenol, Vitamin B6, Vitamin B12, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl) phosphate. In general, retinol, all trans retinoic acid and derivatives, isomers and analogs thereof, are collectively termed "retinoids".

RETINOL, it should be noted, is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Some examples of commercially available products suitable for use herein are Vitamin A Acetate and Vitamin C, both products of Fluka Chemie AG, Buchs, Switzerland; COVI-OX T-50, a vitamin E product of Henkel Corporation, La Grange, Illinois; COVI-OX T-70, another vitamin E product of Henkel Corporation, La Grange, Illinois; and vitamin E Acetate, a product of Roche Vitamins & Fine Chemicals, Nutley, N.J.

The active can be a protein, such as an enzyme. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozymes, superoxide dismutase, catalase, and mixtures thereof. Protease include, but are not limited to, trypsin, chymotrypsin, pepsin, pancreatin and other mammalian enzymes; papain, bromelain and other botanical enzymes; subtilisin, epidermin, nisin, naringinase (L-rhammnosidase) urokinase and other bacterial enzymes. Lipase include, but are not limited to, triacyl-glycerol lipases, monoacyl-glycerol lipases, lipoprotein lipases, e.g. steapsin, erepsin, pepsin, other mammalian, botanical, bacterial lipases and purified ones. In a specific embodiment, natural papain is utilized as the enzyme. Further, stimulating hormones, e.g. insulin, can be used together with the enzyme (s) to boost effectiveness.

The active may also be one or more plant or vegetable extract. Examples of these components are as follows: Ashitaba extract, avocado extract, *hydrangea* extract, Althea extract, *Arnica* extract, aloe extract, apricot extract, apricot kernel extract, *Ginkgo biloba* extract, fennel extract, turmeric[*Curcuma*] extract, oolong tea extract, rose fruit extract, *Echinacea* extract, Scutellaria root extract, Phellodendro bark extract, Japanese Coptis extract, Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, *Artemisia* extract, *Glycyrrhiza* extract, hibiscustea extract, *Pyracantha Fortuneana* Fruit extract, *Kiwi* extract, *Cinchona* extract, cucumber extract, guanocine, *Gardenia* extract, *Sasa Albo-marginata* extract, *Sophora* root extract, Walnut extract, Grapefruit extract, *Clematis* extract, *Chlorella* extract, mulberry extract, *Gentiana* extract, black tea extract, yeast extract, burdock extract, rice bran ferment extract, rice germ oil, comfrey extract, collagen, cowberry extract, *Gardenia* extract, *Asiasarum* Root extract, Family of *Bupleurum* extract, *Salvia* extract, *Saponaria* extract, Bamboo extract, *Crataegus* fruit extract, *Zanthoxylum* fruit extract, *shiitake* extract, *Rehmannia* root extract, gromwell extract, *Perilla* extract, linden extract, *Filipendula* extract, peony extract, *Calamus* Root extract, white birch extract, Horsetail extract, *Hedera helix* (Ivy) extract, hawthorn extract, *Sambucus nigra* extract, *Achillea millefolium* extract, *Mentha piperita* extract, sage extract, mallow extract, *Cnidium officinale* Root extract, Japanese green gentian extract, soybean extract, jujube extract, thyme extract, tea extract, clove extract, *Gramineae imperata* cyrillo extract, Citrus unshiu peel extract Japanese Angellica Root extract, Calendula extract, Peach Kernel extract, Bitter orange peel extract, *Houttuyna cordata* extract, tomato extract, natto extract, *Ginseng* extract, Green tea extract (camelliea sinesis), garlic extract, wild rose extract, hibiscus extract, *Ophiopogon* tuber extract, *Nelumbo nucifera* extract, parsley extract, honey, *hamamelis* extract, *Parietaria* extract, *Isodonis herba* extract, bisabolol extract, Loquat extract, coltsfoot extract, butterbur extract, *Porid cocos* wolf extract, extract of butcher's broom, grape extract, propolis extract, luffa extract, safflower extract, peppermint extract, linden tree extract, *Paeonia* extract, hop extract, pine tree extract, horse chestnut extract, Mizu-bashou [Lysichiton camtschatcese] extract, Mukurossi peel extract, Melissa extract, peach extract, cornflower extract, *eucalyptus* extract, saxifrage extract, citron extract, *coix* extract, mugwort extract, lavender extract, apple extract, lettuce extract, lemon extract, Chinese milk vetch extract, rose extract, rosemary extract, Roman Chamomile extract, royal jelly extract, and combinations thereof.

Representative, non-limiting examples of healthcare actives useful as drugs in the present compositions are described below. One or more of the drugs can be used, either alone or in combination with the actives and/or personal care ingredients described above.

The composition may include an antiparasite agent. The antiparasite agent can be of any type. Examples of antiparasite agents include, but are not limited to, hexachlorobenzene, carbamate, naturally occurring pyrethroids, permethrin, allethrin, malathion, piperonyl butoxide, and combinations thereof.

The composition may include an antimicrobial agent, also referred to as germicidal agent. The antimicrobial agent can be of any type. Examples of antimicrobial agents include, but are not limited to, phenols, including cresols and resorcinols. Such compositions may be used to treat infections of the skin. An example of a very common skin infection is acne, which involve infestation of the sebaceous gland with

*P. acnes*, as well as *Staphylococus aurus* or *Pseudomonas*. Examples of useful antiacne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g. cis and trans); sulfur-containing D and L amino acids and their derivatives and salts, particularly their N-acetyl derivatives, e.g. N-acetyl-L-cysteine; lipoic acid; antibiotics and antimicrobials such as benzoyl peroxide, octopirox, tetracycline, 2,4,4'-trichloro-2'-hydroxy diphenyl ether, 3,4, 4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as symbol sulfate and its derivatives, deoxycholate and cholate; parachlorometaxylenol; and combinations thereof.

Phenols, in concentrations of 0.2, 1.0, and 1.3, % by weight, are generally bacteriostatic, bactericidal, and fungicidal, respectively. Several phenol derivatives are more potent than phenol itself, and the most important among these are the halogenated phenols and bis-phenols, the alkyl-substituted phenols and the resorcinols. Hydrophobic antibacterials include triclosan, triclocarbon, eucalyptol, menthol, methylsalicylate, thymol, and combinations thereof.

The composition may include an antifungal agent. The antifungal agent can be of any type. Examples of antifungal agents include, but are not limited to, azoles, diazoles, triazoles, miconazole, fluconazole, ketoconazole, clotrimazole, itraconazole griseofulvin, ciclopirox, amorolfine, terbinafine, Amphotericin B, potassium iodide, flucytosine (5FC) and combinations thereof. U.S. Pat. No. 4,352,808 discloses 3-aralkyloxy-2,3-dihydro-2-(1H-imidazolylmethyl)benzo[b]thiophene compounds having antifungal and antibacterial activity, which are incorporated herein by reference.

The composition may include a steroidal anti-inflammatory agent. The steroidal anti-inflammatory agent can be of any type. Examples of steroidal anti-inflammatory agents include, but are not limited to, corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amc, amcinafide, betamethasone and the balance of its esters, chlorprednisone, chlorprednisone acetate, clocortelone, clescinolone, dichlorisone, difluprednate, flucloronide, flunisolide, fluorometha-lone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and combinations thereof.

Topical antihistaminic preparations currently available include 1 percent and 2 percent diphenhydramine (Benadryl® and Caladryl®), 5 percent doxepin (Zonalon®) cream, phrilamine maleate, chlorpheniramine and tripelennamine, phenothiazines, promethazine hydrochloride (Phenergan®) and dimethindene maleate. These drugs, as well as additional antihistamines can also be included in the composition. Additionally, so-called "natural" anti-inflammatory agents may be useful. For example, candelilla wax, alpha bisabolol, aloe vera, Manjistha (extracted from plants in the genus *Rubia*, particularly *Rubia cordifolia*), and Guggal (extracted from plants in the genus *Commiphora*, particularly *Commiphora mukul*, may be used as an active in the composition.

The composition may include a non-steroidal anti-inflammatory drug (NSAID). The NSAID can be of any type. Examples of NSAIDs include, but are not limited to, the following NSAID categories: propionic to acid derivatives; acetic acid derivatives; fenamic acid derivatives; biphenylcarboxylic acid derivatives; and oxicams. Such NSAIDs are described in the U.S. Pat. No. 4,985,459, which is incorporated herein by reference. Further examples include, but are not limited to, acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, mniroprofen, tioxaprofen, suprofen, alminoprofen, tiaprofenic acid, fluprofen, bucloxic acid, and combinations thereof.

The composition may include an antioxidant/radical scavenger. The antioxidant can be of any type. Examples of antioxidants include, but are not limited to, ascorbic acid (vitamin C) and its salts, tocopherol (vitamin E), and its derivatives such as tocopherol sorbate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, the ascorbyl esters of fatty acids, amines (e.g. N,N-diethylhydroxylamine, amino-guanidine), sulfhydryl compounds (e.g. glutathione), and dihydroxy fumaric acid and its salts may be used, as well as EDTA, BHT and the like, and combinations thereof.

The composition may include an antibiotic. The antibiotic can be of any type. Examples of antibiotics include, but are not limited to, chloramphenicol, tetracyclines, synthetic and semi-synthesic penicillins, beta-lactames, quinolones, fluoroquinolnes, macrolide antibiotics, peptide antibiotics, cyclosporines, erythromycin, clindamycin, and combinations thereof.

The composition may include a topical anesthetic. The topical anesthetic can be of any type. Examples of topical anesthetics include, but are not limited to, benzocaine, lidocaine, bupivacaine, chlorprocaine, dibucaine, etidocaine, mepivacaine, tetracaine, dyclonine, hexylcaine, procaine, cocaine, ketamine, pramoxine, phenol, pharmaceutically acceptable salts thereof, and combinations thereof.

The composition may include an anti-viral agent. The anti-viral agent can be of any type. Examples of anti-viral agents include, but are not limited to, proteins, polypeptides, peptides, fusion protein antibodies, nucleic acid molecules, organic molecules, inorganic molecules, and small molecules that inhibit or reduce the attachment of a virus to its receptor, the internalization of a virus into a cell, the replication of a virus, or release of virus from a cell. In particular, anti-viral agents include, but are not limited to, nucleoside analogs (e.g. zidovudine, acyclovir, acyclovir prodrugs, famciclovir, gangcyclovir, vidarabine, idoxuridine, trifluridine, and ribavirin), n-docosanoll foscarnet, amantadine, rimantadine, saquinavir, indinavir, ritonavir, idoxuridine alpha-interferons and other interferons, AZT, and combinations thereof.

Additional examples of actives include analgesic agents and antihypertensive agents. Analgesic agents are known in the art and are colloquially referred to as painkillers. The analgesic agent may be selected from any known analgesic agents, and specific examples thereof include paracetamol (acetaminophen), morphine, codeine, heroine, methadone, thebaine, orpiarine, buprenorphine, morphinans, benzomorphans, acetaminophen, butorphanol, diflunisal, fenoprofen, fentanyl, fentanyl citrate, hydrocodone, aspirin, sodium salicylate, ibuprofen, oxymorphone, pentaxicine, naproxen, nalbuphine, mefenamic acid, meperidine and dihydroergotamine, non-steroidal anti-inflammatory agents, such as salicylates, and opioid agents, such as morphine and oxycodone. Antihypertensive agents are known in the art for treating or reducing hypertension, i.e., high blood pressure. The antihypertensive agent may be selected from any known antihypertensive agents, and specific examples thereof include diuretics, adrenergic receptor antagonists (e.g. beta blockers), benzodiazepines, calcium channel blockers, renin inhibitors, etc.

A typical narcotic antagonist is haloxone. Exemplary antitussive agents include, without limitation, diphenhydramine, guaifenesin, hydromorphone, ephedrine, phenylpropanolamine, theophylline, codeine, noscapine, levopropoxyphene, carbetapentane, chlorpehndianol and benzonatate.

Among the sedatives which may be utilized are, without limitation, chloral hydrate, butabarbital, alprazolam, amobarbital, chlordiazepoxide, diazepam, mephobarbital, secobarbital, diphenhydramine, ethinamate, flurazepam, halazepam, haloperidol, prochlorperazine, oxazepam, and talbutal.

Examples of cardiac drugs are, without limitation, quinidine, propranolol, nifedipine, procaine, dobutamine, digitoxin, phenyloin, sodium nitroprusside, nitroglycerin, verapamil HCl, digoxin, nicardipine HCl, and isosorbide dinitrate.

Antiemetics are illustrated by, without limitation, thiethylperazine, metoclopramide, cyclizine, meclizine, prochlorperazine, doxylamine succinate, promethazine, triflupromazine, and hydroxyzine.

A typical dopamine receptor agonist is bromocriptine mesylate. Exemplary amino acid, peptide and protein hormones include, without limitation, thyroxine, growth hormone (GH), interstitial cell stimulating hormone (ICSH), follicle-stimulating hormone (FSH), thyrotropic hormone (TSH), adrenocorticotropic hormone (ACTH), gonadotropin releasing hormone (GnRH) such as leuprolide acetate, vasopressin and their active degradation products Some products may have sufficiently high molecular weights that absorption through the stratum corneum or mucous membranes may be difficult. Therefore, the invention is applicable only to those hormones which have molecular weights and stereo configurations which will allow passage through the skin.

Female sex hormones that can be used include, without limitations, estradiol, diethylstilbestrol, conjugated estrogens, estrone, norethindrone, medroxyprogesterone, progesterone, and norgestrel. Typical male sex hormones that may be utilized may be represented by, without limitation, testosterone, methyltestosterone, and fluoxymesterone.

As introduced above, the emulsion may include various additives (e.g. those added during preparation of the emulsion), such that the emulsion itself functions as an end-use composition. However, the emulsion may also be combined with various additional components (e.g. after its preparation), such as those described above, and thus formulated into various end-use compositions, such as a personal care compositions. Such compositions may be of any form, such as a cream, gel, powder, paste, or freely pourable liquid. Compositions comprising or formed from the emulsion of the present disclosure may exhibit improved application and cosmetic properties (including reduced tackiness and stickiness), and improved clarity/low residue properties.

In some embodiments, the emulsion is itself a personal care composition, or may be formulated into a personal care composition. In such embodiments, the personal care composition may be formulated to be cosmetic, therapeutic, functional with respect to a portion of a body to which the personal care composition is applied, or some combinations thereof. Examples of personal care compositions include antiperspirants and deodorants, skin care creams, skin care lotions, moisturizers, facial treatments (e.g. acne or wrinkle removers), personal and facial cleansers, bath oils, perfumes, colognes, sachets, sunscreens, pre-shave and after-shave lotions, shaving soaps and lathers, shampoos, conditioners, hair colorants, hair relaxants, hair sprays, mousses, hair gels, permanents, depilatories, cuticle coats, make-ups, color cosmetics, foundations, concealers, blushes, lipsticks, eyeliners, mascara, oil removers, color cosmetic removers, and medicament creams, pastes or sprays (e.g. for anti-*acnes*, dental hygienics, antibiotics, healing promotives, etc.). In general, the personal care composition comprising the emulsion is formulated with a carrier that permits application in a conventional form, such as a liquid, rinse, lotion, cream, paste, gel, foam, mousse, ointment, spray, aerosol, soap, stick, soft solid, or solid gel, e.g. depending on the intended use. What constitutes a suitable carrier for formulating the personal care composition is readily apparent to one of ordinary skill in the art, and may be selected from those carriers exemplified herein.

The personal care composition may be in any form, either liquid or non-liquid (semi-solid, soft solid, solid, etc.). For example, the personal care composition may be a paste, a solid, a gel, or a cream. Additionally, regardless of how the emulsion was prepared, the personal care composition formed from the emulsion may itself be an emulsion, such as an oil-in-water or water-in-oil emulsion, a multiple emulsion, such as an oil-in-water-in-oil emulsion or a water-in-oil-in-water emulsion, or a solid, rigid or supple gel, including anhydrous gels. The personal care composition can also be in a form chosen from a translucent anhydrous gel and a transparent anhydrous gel. The personal care composition may, for example, comprise an external or continuous fatty phase. The personal care composition may be anhydrous. In some instances, the personal care composition can be a molded composition or cast as a stick or a dish. In specific embodiments, the personal care composition comprising the emulsion is a molded poured stick. In such embodiments, the personal care composition (e.g. in stick form) may behave as deformable, flexible elastic solid, having increased elastic softness on application.

The personal care composition comprising the emulsion can be used by any method, such as via application to a human body (e.g. skin or hair) by hand or with an applicator (e.g. a brush or sprayer). In some embodiments, the personal care composition may be intended to be removed after such application, e.g. by washing, wiping, peeling, and the like, or combinations thereof.

As mentioned above, the copolymer in general, and specific embodiments of acrylic copolymers in particular, have excellent utility when utilized in or applied as a cosmetic ingredient or film-forming agent, including for quasi-drug formulations or topical formulations. Though not limited to this particular end use application, the inventive copolymer can be utilized instead of or in combination with any conventional copolymer having a carbosiloxane dendrimer structure, which are ubiquitous in existing cosmetic formulations.

For example, the copolymer can partially or fully replace a silicone acrylate copolymer having a carbosiloxane dendrimer structure (e.g. conventional product of FA4001 CM Silicone Acrylate, FA4002 ID Silicone Acrylate, FA4003 silicone Acrylate etc.) in cosmetic formulations in following patent application publications: WO2012/143344, WO2014/154701, WO2014/154700, WO2015/092632, WO2015/097110, WO2015/097103, WO2017/050699, WO2017/050922, WO2010/026538, WO2014/087183, WO2011/051323, JP2007-320960, WO2016/030842, JP2010-018612, JP2011-016734, JP2011-016732, JP2011-016733, JP2011-016734, JP 2011-126807, JP 2011-126808, JP2013-001672, JP 2014-034568, JP 2014-040388, JP 2014-227358, JP2015-098451, JP 2015-137252, JP 2016-008200, JP2016-088848, JP 2016-121095, JP 2016-160191, JP 2018-090495, JP2000-072784, JP07-309714, JP2007-320960, JP2014-040512, WO2017/061090, JP2011-149017, JP2014-040512, JP2014-040511, WO/2018/086139, WO/2018/186138, PCT/JP18/022412, and PCT/JP18/022413.

Specific intended end use applications of the inventive copolymer are based on the cosmetic formulations of the above patent application publications, whereby a conventional copolymer having a carbosiloxane dendrimer structure of these patent application publications is replaced with the inventive copolymer of this disclosure. In certain embodiments, the inventive copolymer is utilized in combination with the conventional copolymer having the carbosiloxane dendrimer structure. In other embodiments, the inventive copolymer is utilized in lieu of (and to replace) the conventional copolymer having the carbosiloxane dendrimer structure.

Furthermore, emulsion compositions comprising copolymers can be partially or fully replaced with the inventive copolymer in emulsion. For example, copolymer emulsions in cosmetic formulations disclosed in the following documents can be replaced with emulsions comprising the inventive copolymers: WO2017/061090, WO/2018/086139, WO/2018/186138, PCT/JP18/022412, PCT/JP18/022413 and Research Disclosures: No. IPCOM000243971D, and No. IPCOM0002457480.

By replacing conventional silicone acrylate copolymer having carbosiloxane dendrimer structure with the copolymer comprising the branched organosilicon moiety in available and conventional cosmetic formulations, the skilled person in the art can anticipate and design similar or improved cosmetic formulation using the copolymer comprising the branched organosilicon moiety.

The following examples, illustrating embodiments of this disclosure, are intended to illustrate and not to limit the invention. The brief summary immediately below provides information as to certain abbreviations, shorthand notations, and components utilized in the Examples. Each group not expressly shown and pending from a silicon atom is a methyl group (—CH$_3$) unless otherwise indicated.

"Si10" is a branched organosilicon compound having 10 silicon atoms and a propyl methacryloxy group, and is of the general formula (a) below:

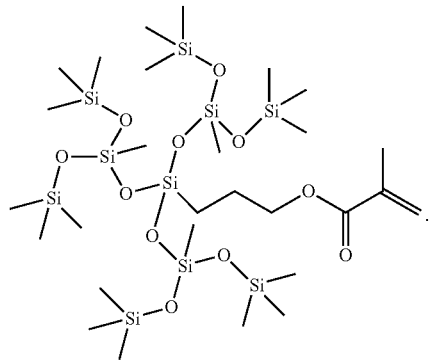

"Artificial Sebum" is 3:1:1 mixed oil of triolein, oleic acid and squalane (wt./wt./wt.).

Preparation of Examples 1-3 and Comparative Example 1

In a first beaker, 0.71 parts by weight of 90% Laureth-1 Phosphate was weighed, and then 51.68 parts by weight of ion exchanged and 0.39 parts by weight of 20% Sodium Hydroxide aqueous solution water were added and agitated to form an aqueous solution. In a second beaker, 0.60 parts by weight of 2-phenoxyethanol, 9.90 parts by weight of methyl methacrylate (MMA), 5.10 parts by weight of butyl acrylate (n-BuA), and 15.00 parts by weight of Si10 were combined and homogenized. The homogenized mixture in the second beaker was then added to the first beaker, and the contents then agitated for several minutes before being passed through a homogenizer (pressure of 300 to 400 kg/cm$^2$) multiple times to obtain a milky white monomer emulsion without oil droplets.

In a third flask, 4.60 parts by weight of ion exchanged water and a portion of the obtained monomer emulsion were combined and heated to 80° C. while the mixture was agitated. Once the temperature reached 80° C., the rest of the obtained monomer emulsion and 7.5 parts by weight of 3% 2,2'-azobis[N-(2-carboxyethyl)-2-methylpropinamidine]tetrahydrate aqueous solution prepared with ion exchanged water were gradually added dropwise simultaneously to allow a reaction to proceed. After 3 hours, 4.5 parts by weight of 5% 2,2'-azobis[N-(2-carboxyethyl)-2-methylpropinamidine]tetrahydrate aqueous solution prepared with ion exchanged water was added. After the reaction, odor of methyl methacrylate or butyl acrylate was not noticeable. The completed emulsion has a nonvolatile content of approximately 30%, and completion of the reaction was confirmed via HPLC (SHIMAZU Prominence-i LC-2030C3D).

The above procedure was repeated using the components and proportions listed in Table 1 below to prepare the emulsions of Examples 1-3 and Comparative Example 1.

TABLE 1

| | Copolymer in Water (emulsion) | | | |
|---|---|---|---|---|
| | Ex. 1 | Ex. 2 | Ex. 3 | Com. 1 |
| Formulation | | | | |
| MMA | 9.9 | 3 | 4.8 | 19.8 |
| n-BuA | 5.1 | 12 | 19.2 | 10.2 |

TABLE 1-continued

| Copolymer in Water (emulsion) | | | | |
|---|---|---|---|---|
| | Ex. 1 | Ex. 2 | Ex. 3 | Com. 1 |
| Si10 | 15 | 15 | 6 | — |
| Laureth-1 Phosphate (90%) | 0.71 | 0.71 | 0.71 | 0.71 |
| 20% NaOH | 0.39 | 0.39 | 0.39 | 0.39 |
| 2-Phenoxyethanol | 0.6 | 0.6 | 0.6 | 0.6 |
| Potassium Persulfate | 0.225 | 0.225 | 0.225 | 0.225 |
| VA-057 | 0.225 | 0.225 | 0.225 | 0.225 |
| Water (for initiator) | 11.39 | 11.39 | 11.39 | 11.39 |
| Water (for flask) | 4.6 | 4.6 | 4.6 | 4.6 |
| Aminomethyl Propanediol Impurity | 0.18 | 0.18 | 0.18 | 0.18 |
| Residual Si10 after 6 hrs | Not detected | Not detected | Not detected | N/A |
| Material Property | | | | |
| Appearance | Flowable White Liquid | Flowable White Liquid | Flowable White Liquid | Flowable White Liquid |
| pH | 6.3 | 6.6 | 6.5 | 6.8 |
| Solid content (wt%) | 30 | 30 | 30 | 30 |
| Film Property | | | | |
| Water Contact Angle (°) | 108 | 111 | 116 | 63 |
| Artificial Sebum contact angle (°) | 63 | 73 | 74 | 23 |
| Film flexibility | OK | OK | OK | NG |

"OK" film flexibility refers to an absence of cracking noticed when bending the film.

"NG" film flexibility refers to a lack of film flexibility/a very hard film.

As shown in Table 1, the composition of the present disclosure enables the preparation of silicone acrylate copolymer emulsions with very low levels of impurities (e.g. low levels of residual Si dendrimer). The film property was also confirmed to be better than non-silicone graft acrylates.

Preparation of Example 4 and Comparative Example 2

In a first beaker, 15.20 parts by weight of methyl methacrylate (MMA), 4.80 parts by weight of butyl acrylate (n-BuA), and 20.00 parts by weight of the acrylate silicone dendrimer (Si10) were combined and mixed homogeneously to give a monomer mixture.

In a second beaker, 0.4 parts by weight of dimethyl 2,2'-azobis(2-methylpropionate) was weighed, and then charged with 21.38 parts by weight of isopropyl alcohol (IPA) and agitated to form a radical initiator solution.

In a third flask, 32.44 parts by weight of isopropyl alcohol (IPA) was charged, heated to 70° C. with agitation, and purged for 30 min via $N_2$ bubbling to remove oxygen from the IPA. After the temperature reaches 70° C., the monomer mixture in the first beaker and the radical initiator solution in the second beaker were gradually added dropwise simultaneously. Once the addition was complete, 6.18 parts by weight of isopropyl alcohol was used to rinse the first and second beakers into the third, and the reaction allowed to proceed for 10 hours at 70° C. The IPA was then replaced with isododecane (IDD) by 110° C. heating in vacuo (50 mmHg vacuum) to give a polymer solution with a nonvolatile content of approximately 40%. Residual Si dendrimer was determined by HPLC (SHIMAZU Prominence-i LC-2030C3D).

The above procedure was repeated using the components and proportions listed in Table 2 below to prepare the compositions of Example 4 and Comparative Example 2.

TABLE 2

| Copolymer in Carrier Vehicle | | |
|---|---|---|
| | Ex. 4 | Com. 2 |
| Formulation | | |
| MMA | 15.2 | 15.2 |
| n-BuA | 4.8 | 4.8 |
| Si10 | 20 | — |
| 3-Methacryloxy-propyltris{[tris(tri-methylsiloxy)silyl]ethyldi-methylsiloxy}silane | — | 20 |
| V-601 | 0.4 | 0.4 |
| IPA | 21.38 + 32.44 + 6.18 | 21.38 + 32.44 + 6.18 |
| IDD | 60 | 60 |
| Rxn Time to reach <0.4% | 8 hrs | >10 hrs |
| Residual Si dendrimer after whole process | 0.15% | 0.41% |
| Material Property | | |
| Appearance | Flowable Clear Liquid | Flowable Clear Liquid |
| Viscosity | 733 mPa · s | 168 mPa · s |
| Film Property | | |
| Water Contact Angle (°) | 112 | 108 |
| Artificial Sebum contact angle (°) | 66 | 65 |
| Film flexibility | OK | OK |
| Tackiness | None | None |

"OK" film flexibility refers to an absence of cracking noticed when bending the film.

The terms "comprising" or "comprise" are used herein in their broadest sense to mean and encompass the notions of "including," "include," "consist(ing) essentially of," and "consist(ing) of. The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples.

Generally, as used herein a hyphen "-" or dash "-" in a range of values is "to" or "through"; a ">" is "above" or "greater-than"; a "≥" is "at least" or "greater-than or equal to"; a "<" is "below" or "less-than"; and a "≤" is "at most" or "less-than or equal to." On an individual basis, each of the aforementioned applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

Further, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The invention has been described in an illustrative manner, and it is to be understood that the terminology which has been used is intended to be in the nature of words of description rather than of limitation. Obviously, many modifications and variations of the present invention are possible in light of the above teachings. The invention may be practiced otherwise than as specifically described.

What is claimed is:

1. A method of preparing a copolymer, said method comprising:
   reacting a branched organosilicon compound and an acrylate-functional compound in the presence of a carrier vehicle;
   wherein the branched organosilicon compound has the following general formula (I):

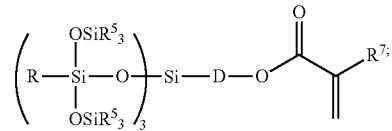

where each R is an independently selected substituted or unsubstituted hydrocarbyl group, D is a divalent linking group, each $R^5$ is selected from R, $-OSi(R^6)_3$, and $-[OSiR_2]_mOSiR_3$; where each $R^6$ is selected from R and $-[OSiR_2]_mOSiR_3$; where $0 \leq m \leq 100$, and $R^7$ is H or R;
   wherein the method prepares a reaction product comprising the copolymer and wherein the method further comprises: (i) isolating the copolymer from the reaction product; (ii) performing a solvent-exchange process with the reaction product; or (iii) both (i) and (ii).

2. The method of claim 1, wherein the branched organosilicon compound and the acrylate-functional compound are reacted in the presence of an initiator to give the copolymer.

3. A copolymer formed in accordance with the method of claim 1.

4. A film formed with the copolymer of claim 3.

5. A composition, comprising:
   a carrier vehicle; and
   a copolymer;
   wherein the copolymer is prepared by reacting a branched organosilicon compound and an acrylate-functional compound;
   wherein the branched organosilicon compound has the following general formula:

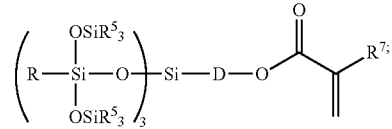

where each R is an independently selected substituted or unsubstituted hydrocarbyl group, D is a divalent linking group, each $R^5$ is selected from R, $-OSi(R^6)_3$, and $-[OSiR_2]_mOSiR_3$; where each $R^6$ is selected from R and $-[OSiR_2]_mOSiR_3$; where $0 \leq m \leq 100$, and $R^7$ is H or R.

6. The composition of claim 5, further defined as at least one of: (i) an emulsion; (ii) an aqueous composition; (iii) an oil composition; (iv) a surfactant composition; (v) a wetting composition; (vi) a film-forming foam; (vii) a surface tension modifier; (viii) an antiblocking additive; (ix) an agricultural composition; (x) a coating composition; (xi) a paint composition; (xii) a surface treating composition; (xiii) a film-forming composition; and (xiv) a cosmetic composition.

7. The composition of claim 5, wherein the carrier vehicle is non-aqueous and wherein the composition further comprises water such that composition is further defined as an emulsion.

8. The composition of claim 5, wherein the carrier vehicle comprises water.

9. The composition of claim 5, wherein each $R^5$ and each R is a methyl group.

10. The composition of claim 5, wherein the branched organosilicon compound and the acrylate-functional compound are reacted in the presence of an initiator to give the copolymer.

11. The composition of claim 5, wherein the copolymer is prepared in a reaction product comprising the copolymer and wherein the copolymer is further prepared by: (i) isolating the copolymer from the reaction product; (ii) performing a solvent-exchange process with the reaction product; or (iii) both (i) and (ii).

\* \* \* \* \*